(12) United States Patent
Mawatari

(10) Patent No.: US 7,036,979 B2
(45) Date of Patent: May 2, 2006

(54) PHOTOTHERMAL TRANSDUCING SPECTROSCOPIC ANALYZER

(75) Inventor: Kazuma Mawatari, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/181,267

(22) PCT Filed: Jan. 29, 2001

(86) PCT No.: PCT/JP01/00574

§ 371 (c)(1),
(2), (4) Date: Jul. 16, 2002

(87) PCT Pub. No.: WO01/55706

PCT Pub. Date: Aug. 2, 2001

(65) Prior Publication Data

US 2003/0002038 A1    Jan. 2, 2003

(30) Foreign Application Priority Data

Jan. 28, 2000    (JP) .............................. 2000-020574

(51) Int. Cl.
*G01N 21/63*    (2006.01)
*G01N 21/71*    (2006.01)
*G01J 5/08*    (2006.01)
*G01J 1/04*    (2006.01)

(52) U.S. Cl. ...................................... 374/130; 356/432
(58) Field of Classification Search .................... 374/5, 374/45, 57, 130, 131; 356/300, 302–303, 356/311, 326, 432, 630, 213, 315, 316, 317
See application file for complete search history.

(56) References Cited

U.S. PATENT DOCUMENTS 4,193,690 A * 3/1980 Levenson et al. ........... 356/301

(Continued)

FOREIGN PATENT DOCUMENTS

EP    1 087 223 A1    3/2001

(Continued)

OTHER PUBLICATIONS

Kovacs et al., "Electrophoretic System", Patent Abstracts of Japan, Japanese Patent Publication No. 02-245655, 1 page, (Oct. 1, 1990).

(Continued)

*Primary Examiner*—Gail Verbitsky
(74) *Attorney, Agent, or Firm*—Finnegan, Henderson, Farabow, Garrett & Dunner, L.L.P.

(57) ABSTRACT

In a photothermal spectroscopic analyzer in which a probe light is made to fall on a thermal lens produced in a sample by an input of an excitation light and the sample is analyzed in accordance with a change of the probe light which is caused by the thermal lens, a light source of excitation light is composed of semiconductor laser light emitting means, and a light source of the probe light is composed of another semiconductor laser light emitting means, and furthermore a condenser lens for focusing the excitation light upon the sample and a condenser lens for focusing the probe light upon the thermal lens are configured by a common condenser lens. Such a photothermal spectroscopic analyzer according to the present invention satisfies all the requirements of small size, low manufacturing cost, high sensitivity, high precision, maintenance free performance, short start-up time, and automatic measurement for such a device as to perform POC analysis.

30 Claims, 5 Drawing Sheets

U.S. PATENT DOCUMENTS

| | | | | |
|---|---|---|---|---|
| 4,521,118 A | * | 6/1985 | Rosencwaig | 374/5 |
| 4,720,176 A | * | 1/1988 | Klein et al. | 350/353 |
| 4,750,822 A | * | 6/1988 | Rosencwaig et al. | 356/445 |
| 4,752,140 A | * | 6/1988 | Cielo et al. | 374/55 |
| 4,790,664 A | * | 12/1988 | Saito et al. | 356/432 |
| 4,872,743 A | * | 10/1989 | Baba et al. | 359/298 |
| 4,938,593 A | | 7/1990 | Morris et al. | |
| 5,074,669 A | * | 12/1991 | Opsal | 356/445 |
| 5,159,412 A | * | 10/1992 | Willenborg et al. | 356/445 |
| 5,228,776 A | * | 7/1993 | Smith et al. | 374/5 |
| 5,243,983 A | * | 9/1993 | Tarr et al. | 128/633 |
| 5,258,612 A | * | 11/1993 | Clark et al. | 250/226 |
| 5,408,327 A | * | 4/1995 | Geiler et al. | 356/432 |
| 5,513,006 A | * | 4/1996 | Schulz et al. | 356/432 |
| 5,619,326 A | * | 4/1997 | Takamatsu et al. | 356/487 |
| 5,645,351 A | * | 7/1997 | Nakata et al. | 374/161 |
| 5,657,119 A | * | 8/1997 | Kawasaki et al. | 356/300 |
| 5,667,300 A | * | 9/1997 | Mandelis et al. | 374/43 |
| 5,706,094 A | * | 1/1998 | Maris | 356/432 |
| 5,963,577 A | | 10/1999 | Lee et al. | |
| 5,974,020 A | | 10/1999 | Ju et al. | |
| 6,271,921 B1 | * | 8/2001 | Maris et al. | 356/432 |
| 6,304,541 B1 | * | 10/2001 | Chang et al. | 369/112.06 |
| 6,375,347 B1 | * | 4/2002 | Bruce et al. | 374/5 |
| 6,490,309 B1 | * | 12/2002 | Okazaki et al. | 372/75 |
| 6,504,618 B1 | * | 1/2003 | Morath et al. | 356/630 |
| 6,515,284 B1 | * | 2/2003 | Walle et al. | 250/341.6 |
| 6,522,413 B1 | * | 2/2003 | Opsal et al. | 356/601 |
| 6,560,478 B1 | * | 5/2003 | Alfano et al. | 600/473 |
| 6,614,532 B1 | * | 9/2003 | Power et al. | 356/432 |
| 6,756,591 B1 | * | 6/2004 | Lounis et al. | 250/316.1 |
| 6,795,180 B1 | * | 9/2004 | Bungo | 356/319 |
| 6,891,618 B1 | * | 5/2005 | Harju et al. | 356/417 |
| 2002/0126732 A1 | * | 9/2002 | Shakouri et al. | 374/130 |
| 2004/0085540 A1 | * | 5/2004 | Lapotko et al. | 356/432 |
| 2004/0196466 A1 | * | 10/2004 | Yamaguchi et al. | 356/432 |
| 2004/0233449 A1 | * | 11/2004 | Yamaguchi et al. | 356/432 |
| 2005/0062971 A1 | * | 3/2005 | Salnik et al. | 356/432 |

FOREIGN PATENT DOCUMENTS

| | | | |
|---|---|---|---|
| EP | 1 211 505 A1 | 6/2002 | |
| JP | 61286725 A | * 12/1986 | 356/FOR. 101 |
| JP | 63 206644 | 8/1988 | |
| JP | 0463938 A1 | * 1/1992 | |
| JP | 09-229883 | 9/1997 | |
| JP | 10142177 A | * 5/1998 | |
| JP | 10-153561 | 6/1998 | |
| JP | 2000-002675 | 1/2000 | |
| JP | 2000-002675 A | 1/2000 | |
| WO | WO 99/64846 | 12/1999 | |
| WO | WO 01/06243 A1 | 1/2001 | |

OTHER PUBLICATIONS

Ueda, "Electrophoresis Device", Patent Abstracts of Japan, Japanese Patent Publication No. 02-259557, 1 page, (Oct. 22, 1990).

Oya, et al., "Photothermal Lens Analyser", Patent Abstracts of Japan, Japanese Patent Publication No. 04-369467, 1 page, (Dec. 22, 1992).

Berthoud, T. et al., "Beam Geometry Optimization in Dual-Beam Thermal Lensing Spectrometry", Anal. Chem., No. 57, pp. 1216-1219, (1985).

Rojas, D. et al., "Thermal Lens Spectroscopy Using a Diode Laser and Optical Fibers", Rev. Sci. Instrum., vol. 63, No. 5, pp. 2989-2993, (May 1992).

Kim, S. H., "Diode-Laser-Based Portable Thermal Lensing Spectroscopy System with Optical Fiber", Bull. Korean Chem. Soc., vol. 18, No. 1, pp. 108-109, (1997).

Forteza, A. C. et al., "Dual-Laser Crossed-Beam Thermal Lens Spectrophotometer Pumped with a Semiconductor Diode-Array Laser", Anal. Chimica Acta., No. 282, pp. 613-623, (1993).

Nakanishi, K. et al., "Thermal Lens Spectorphotometry of Phosphorus Using a Near-Infrared Semiconductor Laser", Anal. Chem., vol., 57, No. 7, pp. 1219-1223, (1985).

Kim, S. H. et al., "Design of Simple and Compact Thermal Lensing Spectroscopy System with Visible Diode Laser", Bull. Korean Chem. Soc. vol. 17, No. 6, pp. 536-538, (1996).

Tokeshi, M. et al., "Single- and Countable-Molecule Detection of Non-Fluorescent Molecules in Liquid Phase", Journal of Luminescence, No. 83-84, pp. 261-264, (1999).

McCormick, R. M. et al., "Microchannel Electrophoretic Separations of DNA in Injection-Molded Plastic Substrates", Anal. Chem. vol. 69, No. 14, pp. 2626-2630, (Jul. 15, 1997).

Mladen Franko et al., "Analytical thermal lens instrumentation," Review of Scientific Instruments, vol. 67, No. 1, 1996, pp. 1-18.

* cited by examiner

PHOTOTHERMAL TRANSDUCING SPECTROSCOPIC ANALYZER

TECHNICAL FIELD

The present invention relates to a small and inexpensive photothermal spectroscopic analyzer which analyzes a microvolume sample in high sensitivity by using a semiconductor laser.

BACKGROUND ART

The importance has been noted of carrying out analysis and measurements right at the site or in the vicinity of the site where analysis and measurements are required (hereinafter referred to as "POC (point of care) analysis etc."), such as analysis for bedside diagnosis which carry out measurements necessary for a medical diagnosis at the patient's side (POC analysis), analysis of toxic substances in rivers or wastes carried out at the sites, that is, on rivers, waste disposal centers and the like, and tests for contamination carried out at the site of cooking foods, harvesting crops, or importing foods. Then, importance has been attached to the development of detection methods and detection apparatus which are applied to such POC analysis etc. in recent years.

In the detection method and detection apparatus which are applied to such POC analysis etc., it is required that an analysis is simple, brief, and inexpensive. Furthermore, in a medical diagnosis or an environmental analysis, in order to perform comparison with a reference value, which a national government defines, in sufficient precision, it is generally required that a high sensitivity analysis is performed.

Recently, μ-TAS (micro total analysis system), which has a groove, whose depth is from tens μm to hundreds μm, on a flat glass or silicon chip at the largest 10 by 10 cm square in dimensions, or a few by few cm square or smaller in dimensions, and performing all of reactions, separation, and detection for a short time in this groove has been actively studied (for example, Japanese Patent Laid-Open No. 2-245655).

The adoption of μ-TAS has advantages that the amounts of samples, reagents for detection, and waste materials and waste fluid of consumables used for the detection are reduced, and necessary detection time is also short in general.

In addition, a method of forming a chip with resin(R. M. Mccormick et al., Anal. Chem., vol. 69, 2626–2630, 1997, Japanese Patent Laid-Open No. 2-259557, and Japanese Patent No.2639087 (registered on Apr. 25, 1997 for Shimadzu Corp.)) for developing an inexpensive disposable chip is also proposed.

However, since optical path length is dozens to hundreds μm that is 1/10 to 1/100 of that under usual conditions, in inverse proportion to it, it is required that the sensitivity of a detection apparatus is 10 to 100 times as high as that under usual conditions when optically detecting a measuring object in μ-TAS.

Up to now, a photoinduced fluorescence method or a chemiluminescence method which use a luminescence phenomenon from a measuring object and analyze the concentration and the like of the measuring object from the quantity of light of its luminescence have been adopted in a highly sensitive apparatus which optically detects the measuring object. However, the photoinduced fluorescence method has a problem that background becomes large by fluorescence from other objects than a measuring object in practical samples with many impurities since the light with wavelength near an ultraviolet ray is generally used in many cases as a light source to excite the measuring object. In addition, since a measuring object is limited to fluorescent material, it is not general as a detection method in clinical inspection such as an analysis of blood components.

Furthermore, although there is an advantage that the chemiluminescence method does not need a light source for excitation, it has not versatility similarly to the photoinduced fluorescence method.

On the other hand, as a general detection method, there is an absorption photometry which analyzes the concentration and the like of a measuring object by the absorbance of light.

Since the absorption photometry is a method applicable to any object so long as it absorbs the light with wavelength for excitation, it has been used as a detection method with very high versatility.

In addition, since the sensitivity of absorption photometry is low in comparison with the photoinduced fluorescence method or chemiluminescence method, the concentration sensitivity of the absorption photometry has been increased by providing dozens mL of measuring object, which is sufficient quantity, and making optical path length be 1 cm which is long. However, in μ-TAS, since the optical path length becomes 1/10 to 1/100 as described above, the absorption photometry has a problem that sensitivity is low when it is applied to μ-TAS although it is a common and highly versatile detection method.

As detection methods which solve the above-described problems simultaneously, photothermal spectroscopy methods are mentioned. These detection methods are methods of utilizing a phenomenon of a measuring object absorbing light that is usually a laser beam with the same wavelength as the absorption wavelength of the measuring object (hereafter, this light will be described as excitation light), and emitting heat (photothermal effect) to a surrounding solvent following relaxation process, and analyzing the concentration and the like of the measuring object by measuring the heat. The photothermal spectroscopy methods have a characteristic that the amount of absorption of light, i.e., the heat can be directly measured against the absorption photometry indirectly measuring the amount of absorption of light as the amount of decrease of transmitted light.

Among such methods, a thermal lens spectrometry of using a thermal lens effect is also known as a most sensitive detection method. When a laser beam is focused with a condenser lens and is incident on a measuring object, heat generates near its focus (focal point) by the above-described photothermal effect, and temperature at the point rises. Since the spatial intensity distribution of the laser beam in the above-described focus is generally a gaussian type, the heat distribution, generated in proportion to the intensity distribution, and the temperature distribution generated as its result also become gaussian types. Then, since a refractive index of a solvent decreases as temperature rises, the refractive index distribution becomes a reversal gaussian type. Since this refractive index distribution can be assumed to be equivalent to a concave lens optically, and such refractive index distribution is called a thermal lens. This thermal lens spectrometry has another excellent characteristic that this method has 100 times or more of sensitivity as high as that of the absorption photometry in addition to a characteristic that a measuring object should just absorb the light with wavelength for excitation similarly to the absorption photometry.

In such a thermal lens spectrometry, there are a single beam method of performing both the excitation and detection of a thermal lens with one laser, and a double beam method using two separate lasers for excitation and detection of a thermal lens. Although the single beam method is characterized in simple structure and easy optical adjustment, it becomes difficult to set the optimal optical configuration for each of excitation and detection since one laser performs both the excitation and the detection of a thermal lens, and sensitivity is low in comparison with the double beam method.

On the other hand, since the double beam method can use separate lasers for the excitation and the detection of a thermal lens, it is possible to set the optimal optical configuration for each, and to realize high sensitivity. Then, many examples of such a double beam method are known.

In addition, there is an example where highly sensitive measurement was performed with applying this double beam method to μ-TAS (Manabu Tokeshi et al., J. Lumin., Vol.83–84, 261–264, 1999). In this double beam method, an Ar ion laser is used as an excitation light source, and a helium neon laser is used as a detection light source (hereafter, detection light is described as probe light), after making these two laser beams coaxial, the beams are led to a microscope, and are focused with an objective lens on a sample in a groove engraved on a chip.

In such a conventional thermal lens spectrometry, a gas laser such as an Ar ion laser or a helium neon laser, a dye laser excited by a gas laser, or the like has been generally used. However, presently, when an apparatus generating the above-described laser beams is actually used, the apparatus is large-sized, large-scale cooling means such as water cooling means is needed at the time of a high-power output, and the apparatus becomes very expensive. In order to solve those problems, several examples that use semiconductor lasers and are comparatively small systems are known.

First, examples using the single beam method will be described. In Japanese Patent Laid-Open No. 4-369467, a semiconductor laser is used, further, in order to shorten distance between a sample and a detector, an optical system which detects a focus error of reflected light is adopted, and the miniaturization of an optical head is realized.

In addition, there is also an example where an apparatus which is small and portable is realized with the single beam method using the semiconductor laser with a wavelength of 670 nm, and further, an entire system is miniaturized by connecting a sample and a detector with a fiber (KIM S-H, Bull. Korean Chem. Soc., Vol. 18, 108–109, 1997, and KIM S -H et al., Bull. Korean Chem. Soc., Vol. 17, 536–538, 1996).

On the other hand, there is also an example using the double beam method. For example, phosphorus was analyzed by making a semiconductor laser with a wavelength of 824 nm be an excitation light source, and the detection limit of 0.35 ppb was obtained in an aqueous solution (K. Nakanishi et al., Anal. Chem., Vol. 57, 1219–1223, 1985).

FIG. 7 shows a structural diagram explaining the construction of a conventional photothermal spectroscopic analyzer using the double beam method which uses semiconductor lasers. In such a photothermal spectroscopic analyzer, excitation light is outputted from a semiconductor laser beam-emitting apparatus 71, and after being focused with a lens 72, the light is focused with a condenser lens 73 on a sample in a glass sample cell 75 with the optical path length of 1 cm. Then, a thermal lens is formed in the above-described sample where the above-described excitation light is incident.

In addition, probe light outputted from a helium neon laser apparatus 81 is led to the sample cell 75 by a beam splitter 74 in collimated light coaxially with the above-described excitation light. The probe light incident on the above-described thermal lens is given a thermal lens effect in the sample cell 75, reflected by a mirror 76, and focused by a condenser lens 77, and thereafter, the probe light is received by a photodiode 80 through an excitation light cut-off filter 78 and a pinhole 79, and is given a signal analysis.

Similarly, there is also an example where the detection limit of $8\times10^{-5}$ M is obtained with using $Nd^{3+}$ aqueous solution and a 10mW excitation light output by using a GaAlAs semiconductor laser with the wavelength of 795 nm as an excitation light source (D. Rojas et al., Rev. Sci. Instrum., Vol. 63, 2989–2993, 1992).

Furthermore, in order to improve sensitivity, there is also an example where the absorbance limit of $1.1\times10^{-3}$ was obtained in an aqueous solution by increasing an output of excitation light to 100 mW by using an array type semiconductor laser with the wavelength of 818 nm (Cladera Forteza et al., Anal. Chem. Acta Vol. 282, 613–623, 1993).

However, each of these three examples uses a helium neon laser, which is comparatively large-sized and expensive, as probe light, and hence, this is not an apparatus composed of only semiconductor lasers.

As mentioned above, the photothermal spectrocopy method is highly sensitive in comparison with the absorption photometry which analyzes a sample by using the absorption of light similarly, and it is possible to miniaturize a photothermal spectroscopic analyzer to some extent by making a semiconductor laser be an excitation light source.

However, the above-described conventional technology has the following problems when realizing the photothermal spectroscopic analyzer which is equipped with high sensitivity, high accuracy, maintenance-free performance, short start-up time, and high reliability and operability in addition to the natural requirements for performing a POC analysis etc., that is, small dimensions for portable use and inexpensiveness.

First, as mentioned above, the single beam method using a semiconductor laser has an advantage that the adjustment of an optical system becomes easy. However, since its sensitivity is low in comparison with the double beam method, its sensitivity is insufficient in many cases as a method of using this in the case, where high accuracy is required in data, such as medical diagnosis or an environmental analysis.

Next, in the conventional double beam method, only an excitation light source is composed of a semiconductor laser, and a helium neon laser that is large-sized and expensive is still used as a probe light source. In such a case, it is reported that the minimum size of an optical system except the light sources is 30 cm×30 cm. However, since the size of the helium neon laser which is a light source is usually 5 cm dia.×20 cm long, the apparatus become large-sized when this is added (D. Rojas et al., Rev. Sci. Instrum., Vol. 63, 2989–2993, 1992).

In addition, since a large-sized laser such as a helium neon laser is used, a light source and an optical system cannot be integrated and the light source and optical system are separately fixed on an optical bench, and hence, carrying is impossible. Furthermore, a gas laser also has troubles such as necessity of a high voltage power supply.

Moreover, up to now, in order to obtain sufficient measurement sensitivity, it is necessary to make distance from a sample to a device corresponding to a pinhole be 1 m or more that is long. Thus, since long distance is necessary for leading the probe light, which is given the thermal lens effect in the sample, to a pinhole, the miniaturization of the whole optical system is disturbed due to the restriction of such distance from the sample to the device. If this distance is shortened without design, it is expected that it leads to sensitivity deterioration.

In addition, there is an example where the above-mentioned distance is shortened by not using the pinhole method as the light-receiving method but adopting a method using an optical system which directly detects a focus error. However, there is no report of affirming that the sensitivity of this method is superior to that of the pinhole method (Japanese Patent Laid-Open No. 4-369467 applied by YOKOGAWA ELECTRIC CORP.).

Furthermore, as a method of improving the sensitivity of a thermal lens spectrometry, it is commonly known that it is important to optimize the degree of focusing to the depth of a sample cell (namely, optical path length) and to adjust a focal point of probe light with shifting the focal point from a sample (Thierry Berthoud et al., Anal. Chem., Vol. 57, 1216–1219, 1985). However, since the optimal degree of focusing or the optimal focal point of probe light depend on a plurality of other parameters and it is not possible to theoretically analyze all of those parameters systematically, there is no report of the theoretical analysis of the optimum values at the time of raise the degree of focusing, up to now.

In particular, since the optical path length becomes short in µ-TAS, it is expected that it is necessary to raise the degree of focusing to some extent. In order to raise the degree of focusing, it is needed to make the numerical aperture of a condenser lens large. Since a focal length becomes short to several cm when the numerical aperture is increased, it is not possible to make the excitation light and probe light be coaxial due to a spatial limitation in the case that the degree of focusing and the focal point of the probe light are adjusted by using separate condenser lenses for the excitation light and the probe light like a conventional way.

Then, it becomes possible to use a condenser lens with large numerical aperture since the excitation light and probe light are focused after being made to be coaxial if the condenser lens of the excitation light and probe light are made to be common like another conventional technology (Manabu Tokeshi et al., J. Lumin., Vol.83–84, 261–264, 1999). However, there is no report about an adjusting method of a focal point of probe light at the time of sharing a condenser lens.

In particular, since it is known that the outgoing light of a semiconductor laser completely differs from a gas laser, a simple method of adjusting a focal point that is suitable to the characteristics of the semiconductor laser is needed.

First, the outgoing light of a semiconductor laser is divergent light, and its cross sectional geometry becomes elliptic. Furthermore, if the outgoing light is focused as it is, the astigmatism that a focal point changes according to a cross sectional direction of focused light exists. Therefore, when using semiconductor lasers as both the light sources of the excitation light and probe light, it is necessary to correct the intrinsic characteristics of the outgoing light of these semiconductor lasers.

Thus, in the case of using semiconductor lasers as both the light sources of the excitation light and probe light, it is necessary to perform the above-described correction and to provide simple and inexpensive means for adjusting a focal point of the probe light.

In addition, when the numerical aperture of a condenser lens is made large and the degree of focusing is raised, it is necessary to accurately adjust the focal points of the excitation light and probe light in a sample cell. Up to now, since the positional relation of a focal point and a sample cell is visually adjusted by using a microscope, not only a visual alignment error arises, but also an alignment error by a measuring operator is included. In addition, it is impossible to automatically adjust an above-described positional relation with a machine in such visual method. Furthermore, an apparatus becomes large by using a microscope.

In addition, since not only about 10 minutes of time was necessary until being stabilized after switching on a power supply but also mechanical modulation means such as a chopper was required for a gas laser at the time of modulating an output, it was not so easy to perform miniaturization and cost reduction.

Furthermore, in addition to these, it is required that a photothermal spectroscopic analyzer used for POC analysis etc. should be strong in an environmental temperature change and vibration. Furthermore, it is desirable that the photothermal spectroscopic analyzer used for POC analysis etc. does not need a high voltage power supply and is able to be driven by a dry cell etc.

As described above, in conventional technologies, there is no measure for the characteristics naturally required of the photothermal spectroscopic analyzer used for POC analysis etc.

Then, a task of the present invention is to provide a photothermal spectroscopic analyzer which is equipped with all the requirements as an apparatus for POC analysis etc., such as small size, inexpensiveness, high sensitivity, high accuracy, maintenance-free performance, short start-up time, and possibility of automatic measurement by solving the problems which the above conventional photothermal spectroscopic analyzers have.

DISCLOSURE OF THE INVENTION

In order to solve the above-described tasks, the present invention has the following construction. Namely, a photothermal spectroscopic analyzer of the present invention is a photothermal spectroscopic analyzer in which probe light is incident on a thermal lens generated in a sample by the incidence of an excitation light, and analyzes the above-described sample on the basis of a change of the probe light by the above-described thermal lens in that case, and is characterized in that a light source of the above-described excitation light consists of semiconductor laser beam-emitting means, that a light source of the above-described probe light consists of another semiconductor laser beam-emitting means, and that a condenser lens which focuses the above-described excitation light in the above-described sample and a condenser lens which focuses the above-described probe light in the above-described thermal lens are made to be a common condenser lens.

When the construction is like this, it is possible to make it be a very small and inexpensive photothermal spectroscopic analyzer since both the light source of the above-described excitation light and the light source of the above-described probe light consist of semiconductor laser beam-emitting means. Hence, it is possible to make them be a small-sized unit whose size is about 15 cm×15 cm by integrating the above-described light source and an optical system including the above-described condenser lens in stead of separately fixing them on an optical bench. In addition, it is possible to make its construction very strong in external vibration by integrating optics such as a light source and an optical system to make them a unit.

Furthermore, since the life of a semiconductor laser is about 10 times longer than that of a gas laser, the interval of maintaining a light source can be lengthened sharply.

Furthermore, since the condenser lens which focuses the above-described excitation light, and the condenser lens which focuses the above-described probe light are made to be a common lens, a space for making the above-described semiconductor laser beam, which are emitted from a light source of the above-described excitation light and a light source of the above-described probe light, be coaxial can be sufficiently secured in comparison with the case where the above-described condenser lenses are not common like conventional technology. Therefore, since it is possible to use a lens with high numerical aperture as the above-described condenser lens, and in consequence, it is possible to tightly focus the above-described semiconductor laser beam and to make it incident on the sample, it is also possible to perform high sensitivity analysis even with μ-TAS having short optical path length.

In addition, as for the photothermal spectroscopic analyzer of the present invention, it is good to set both the beam diameters in focal points of the above-described excitation light and above-described probe light, which are focused with the above-described condenser lens, in 0.2 to 50 μm.

Up to now, although investigation about the degree of focusing of excitation light has been performed qualitatively, the effect of improvement in the degree of focusing the probe light has not been considered at all. In the present invention, it was possible to improve the sensitivity in an absorbance and to remarkably shorten the distance from a sample to a device, which was equivalent to a pinhole, in comparison with conventional technology by using a common condenser lens and improving the degree of focusing of probe light.

In conventional technology, even if it aimed at the miniaturization of an apparatus, the beam diameter of excitation light was about 50 μm at a minimum, and that of probe light was about 200 μm at a minimum. In this case, in order to obtain sufficient sensitivity, the necessary distance from a sample to a pinhole was about 2 m (Thierry Berthoud et al., Anal. Chem., Vol. 57, 1216–1219, 1985). Since it was expected that the sensitivity would remarkably fall if this distance was shortened, this distance restricted the miniaturization of a whole optical system.

In addition, by using a turn-back mirror etc., it is possible to make the distance from a sample to a pinhole be sufficient length and also to miniaturize an optical system to some extent. However, there is a problem that there is a bad influence by the pointing noise of a laser beam in this case. This pointing noise is noise deriving from the fluctuation of an optical axis of a laser beam, and since optical path length does not change even if a turn-back mirror etc. is used, this noise level does not fall.

In the present invention, it became possible to remarkably shorten the distance from a sample to a pinhole without spoiling sensitivity by making condenser lenses of excitation light and probe light common to make the beam diameter of a probe light made sufficiently smaller than that in conventional technology in a focal point. Since the above-described distance is short, the pointing noise becomes small in proportion to a shortened part of the distance. Thus, while realizing improvement in an S/N ratio (Signal-to-Noise ratio) where the pointing noise is made small with maintaining high sensitivity by improving the degree of focusing of the probe light, the miniaturization of the whole optical system is attained.

Furthermore, the photothermal spectroscopic analyzer of the present invention can be configured by comprising at least detection means out of detection means of detecting a change of the above-described probe light by the above-described thermal lens, and transmission means which is arranged between the above-described sample and above-described detection means, for making a part of the above-described probe light, which is changed by the above-described thermal lens, transmit, the distance in the direction of an optical axis between the transmission means and the above-described sample is set at 10 cm or less when it has the above-described transmission means, and the distance in the direction of an optical axis between the above-described detection means and the above-described sample is set at 10 cm or less when it does not have the above-described transmission means.

Since the condenser lens is shared between excitation light and probe light and the degree of focusing of the above-described probe light is improved, the distance in the direction of an optical axis between the above-described detection means or the above-described transmission means, and the above-described sample can be set at 10 cm or less without spoiling sensitivity, and hence, it is possible to miniaturize the whole optical system to the size of enabling carrying. In addition, as the above-described transmission means, for example, a device equivalent to a pinhole can be cited.

Furthermore, in the double beam method, since it was known that sensitivity was improved when a focal point of probe light was shifted from a focal point of excitation light by predetermined distance, adjustment means of the above-described distance was provided. In conventional technology, since separate condenser lenses were used for excitation light and probe light, the above-described distance was adjusted by moving a location of the condenser lens, which focuses the probe light, in the direction of an optical axis.

However, the above-described technique cannot be applied when a condenser lens is shared between the excitation light and probe light like the present invention. In addition, since further addition of a lens for adjusting a focal point of the probe light increases the number of parts and the time and effort of adjustment in relation to it, it becomes the hindrance of cost reduction. Furthermore, as described above, since the outgoing light of a semiconductor laser beam is emitted with elliptically diverging, a correction mechanism which corrects this is needed.

Then, the photothermal spectroscopic analyzer of the present invention can be equipped with at least one out of a collimator lens where a semiconductor laser beam emitted from a light source of the above-described excitation light is incident, and a collimator lens where a semiconductor laser beam emitted from a light source of the above-described probe light is incident.

Since a semiconductor laser beam which is divergent light can be brought close to collimated light by the above-described collimator lens in such construction, it is possible to suppress power loss in the condenser lens, and to improve the degree of focusing by the condenser lens when it is brought close to collimated light, and hence, it is possible to improve the sensitivity of the photothermal spectroscopic analyzer.

Furthermore, it is possible to improve the sensitivity of the photothermal spectroscopic analyzer since it becomes possible to adjust a focal point of the probe light by providing the collimator lens with shifting it in the direction of an optical axis from a location where the semiconductor laser beam becomes the collimated light. Furthermore, since a parts count can be reduced to the minimum, the photothermal spectroscopic analyzer can be made inexpensive.

In addition, since the adjustment of a focal point of probe light is the adjustment of the distance between the focal point of probe light and a focal point of excitation light, it is good to install a collimator lens, where the semiconductor laser beam emitted from the light source of excitation light is incident, so that the excitation light may be focused at a location which is apart by predetermined distance from the focal point of probe light.

Furthermore, the photothermal spectroscopic analyzer of the present invention can be configured so as to be equipped with focal point adjustment means in at least one collimator lens out of the above-described collimator lenses for adjusting a focal point of the above-described semiconductor laser beam by changing the distance in the direction of an optical axis between the collimator lens and the above-described light source.

In such a construction, when the above-described semiconductor laser beam-emitting means is exchanged by its life etc., an error derived from inter-lot difference of an angle of divergence or wavelength can be adjusted, or when the above-described angle of divergence from the above-described semiconductor laser beam-emitting means changes with time, it is possible to perform adjustment and optimization.

Furthermore, the photothermal spectroscopic analyzer of the present invention can be equipped with rounding means between at least either a light source of the above-described excitation light or a light source of the above-described probe light, and the above-described condenser lens of bring close the cross sectional geometry of the semiconductor laser beam emitted from the above-described light source in the shape of a perfect circle.

In such a construction, since it is possible to bring the cross sectional geometry of a semiconductor laser beam close to a perfect circle from an ellipse, it is possible to eliminate anisotropy of the cross section (cross section along a plane perpendicular to the direction of an optical axis) of beam diameter in a focal point. Therefore, since the beam diameter can be specified uniquely, the optimization of the beam diameter becomes easy.

Furthermore, the photothermal spectroscopic analyzer of the present invention can be equipped with astigmatism correction means between at least either a light source of the above-described excitation light or a light source of the above-described probe light, and the above-described condenser lens for reducing the astigmatism of the semiconductor laser beam, emitted from the above-described light source.

In such a construction, since it is possible to correct the astigmatism that a semiconductor laser beam originally has, it is possible to eliminate the anisotropy in the cross section of beam diameter in a focal point. Therefore, since a focal point can be specified uniquely, the optimization of the focal point becomes easy.

Furthermore, in the photothermal spectroscopic analyzer of the present invention, alight source of the above-described excitation light and a light source of the above-described probe light can be also made of semiconductor laser beam-emitting means of being output-controllable.

In such a construction, since it is possible to perform the output control which is a characteristic of the semiconductor laser beam-emitting means, stable measurement with few noise is attained. In addition, a gas laser usually requires about 10 minutes from start-up to the stabilization of temperature, and in consequence, the stabilization of an output, and tends to be influenced by a change in external temperature. However, in the photothermal spectroscopic analyzer having such construction as described above, it is possible to have one minute or less of start-up time by controlling an output directly even if a temperature change happens, and it is hard to be influenced by a change in external temperature.

Furthermore, in the photothermal spectroscopic analyzer of the present invention, it is preferable to set the wavelength of the above-described excitation light at 400 to 700 nm.

In such a construction, it is possible to decrease background noise, caused by water absorption generated because near-infrared light with the wavelength of about 780 nm is used for excitation light up to now, by approximately one figure, and hence, it is possible to enhance the accuracy of measurement.

Furthermore, in the photothermal spectroscopic analyzer of the present invention, alight source of the above-described excitation light can be also made of semiconductor laser beam-emitting means where electric modulation can be performed.

In such a construction, since mechanical modulation means such as a chopper required in a conventional gas laser become unnecessary, problems of generating physical vibration, upsizing an optical system, and increasing apparatus cost, which are caused by installing mechanical modulation means never arise.

Furthermore, the photothermal spectroscopic analyzer of the present invention may be also equipped with signal extraction means by synchronous detection.

In such construction, since it becomes possible by using the above-described electric modulation to perform highly precise signal extraction with a lock-in amplifier etc., it is possible to enhance the accuracy of measurement.

Furthermore, the photothermal spectroscopic analyzer of the present invention may be also equipped with means of adjusting the distance between at least anyone of focal points of the above-described excitation light and the above-described probe light, and the above-described sample cell which contains the above-described sample by using the light reflected from the above-described sample cell.

In such a construction, since it is possible to quantify the positional relation of the focal points of excitation light and probe light, and a sample cell by using the light reflected from the sample cell, it becomes possible to perform the highly precise adjustment of a location which is needed when a condenser lens with large numerical aperture is used. In addition, since the above-described positional relation can be quantified, it is possible to automate the adjustment of a location of a sample cell after installing the sample cell in the photothermal spectroscopic analyzer.

BEST MODE FOR CARRYING OUT THE INVENTION

Embodiments of a photothermal spectroscopic analyzer according to the present invention will be described in detail with referring to drawings.

Figure 1:
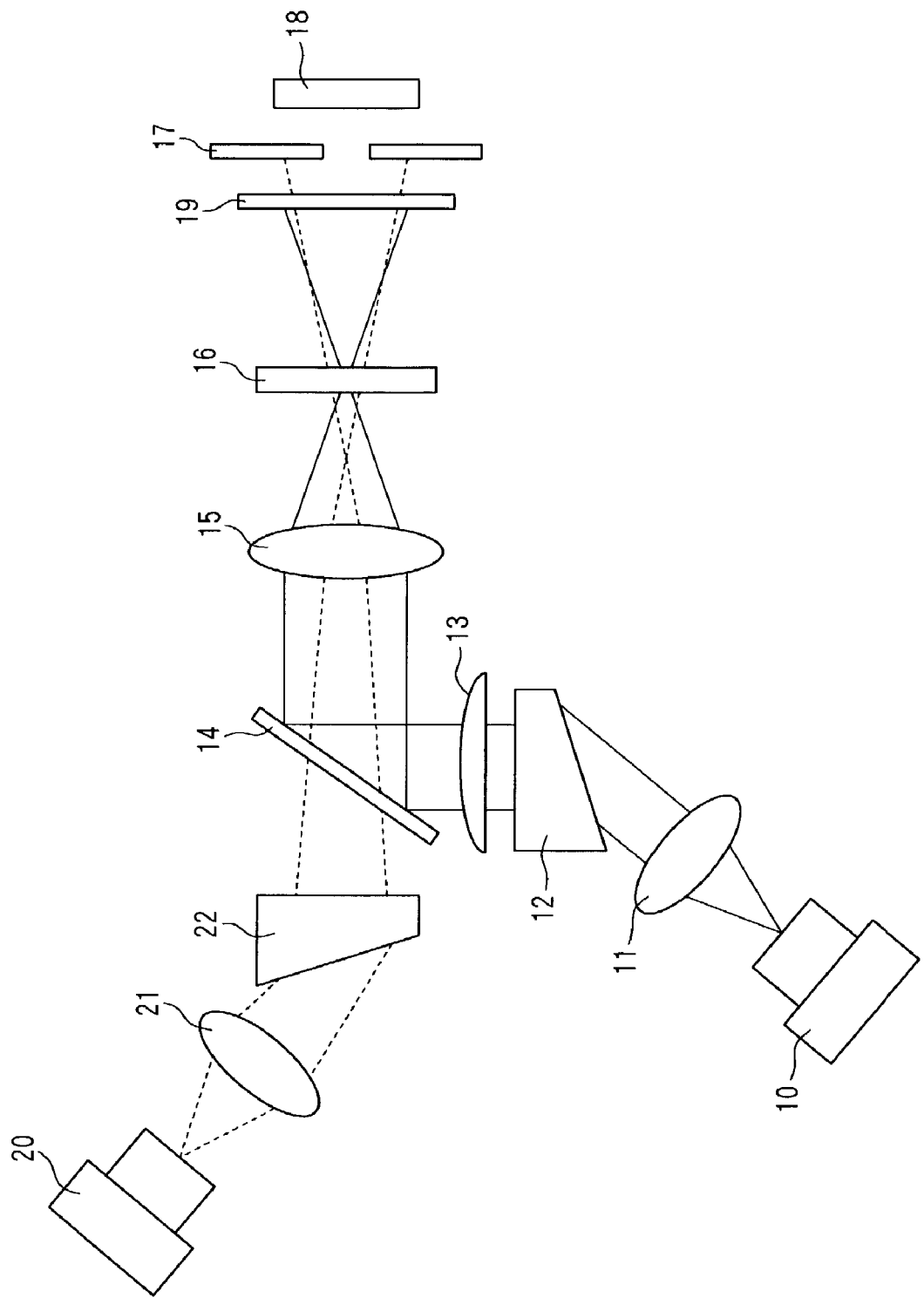
FIG. 1 is a structural diagram showing a embodiment of a photothermal spectroscopic analyzer of the present invention.

FIG. 1 is a structural diagram explaining the construction of a photothermal spectroscopic analyzer according to an embodiment. In addition, this embodiment shows an example of the present invention, and the present invention is not limited to this embodiment.

The photothermal spectroscopic analyzer in FIG. 1 comprises: semiconductor laser beam-emitting means 10 which is a light source of excitation light; semiconductor laser beam-emitting means 20 which is a light source of probe light; a sample cell 16 where a sample is installed; a focusing optical system which consists of collimator lenses 11 and 21 for the above-described excitation light and the above-described probe light, a condenser lens 15 which focuses the above-described excitation light in the above-described sample and focuses the above-described probe light to a thermal lens, and the like; a light-receiving optical system which consists of a filter 19 and a pinhole 17, and detection means 18 which detects a degree of divergence or convergence of the above-described probe light caused by the above-described thermal lens.

In such a photothermal spectroscopic analyzer, excitation light is outputted from the semiconductor laser beam-emitting means 10, and it is converted into approximately collimated light by the collimator lens 11 for excitation light. Then, after passing a prism 12 and a cylindrical lens 13 (astigmatism correction means) which corrects astigmatism, it is focused in the above-described sample, which is installed in the sample cell 16, by the condenser lens 15, and a thermal lens which is not shown is formed in the above-described sample.

In addition, probe light outputted from the semiconductor laser beam-emitting means 20 is converted into approximately collimated light by the collimator lens 21 for probe light. Then, it passes a prism 22, is made coaxial with the above-described excitation light by a beam splitter 14, and is focused in the above-described thermal lens by the condenser lens 15. The above-described probe light which is incident on the above-described thermal lens formed in the above-described sample is given a thermal lens effect within the sample cell 16, passes a filter 19 and a pinhole 17, is received by the detection means 18, and is given signal analysis.

In addition, as the semiconductor laser beam-emitting means 10 and 20, semiconductor laser beam-emitting apparatuses or the like are used, and a photodiode or the like is usually used as the detection means 18.

Then, in this photothermal spectroscopic analyzer, since the collimator lens 21 for probe light can be displaced in the direction of an optical axis of the probe light, the distance between the semiconductor laser beam-emitting means 20 and the collimator lens 21 for probe light can be changed. When the above-described distance is changed by displacing the collimator lens 21 for probe light, a focal point of the probe light is displaced, and hence, the collimator lens 21 for probe light is displaced so that the probe light may focus in the most preferable location (location where measurement can be performed in high sensitivity) in the above-described thermal lens, and thereafter, the collimator lens 21 for probe light is fixed.

In addition, the above-described distance may be changed by displacing the semiconductor laser beam-emitting means 20 instead of the collimator lens 21 for probe light, or the above-described distance may be changed by displacing both.

Furthermore, similarly, also in the excitation light, a focal point of the excitation light may be made controllable to a focal point of the probe light by making at least any one of the semiconductor laser beam-emitting means 10 and the collimator lens 11 for excitation light displaceable.

Hereafter, each part of the photothermal spectroscopic analyzer in FIG. 1 will be individually described.

(With Respect to Semiconductor Laser)

Although the wavelength of a semiconductor laser used as excitation light is acceptable so long as it is within a range where a sample has a certain amount of absorption, it is desirable that it coincides with the maximum absorption wavelength of the sample.

However, it is known that, when an analysis of an aqueous solution is performed by using light with the wavelength of about 780 nm as excitation light like the conventional, in this wavelength region, a background signal that originates in water absorption and cannot be disregarded arises, and hence the accuracy of measurement falls. Therefore, as for the wavelength region of the excitation light, it is desirable to use a visible light region of 400 to 700 nm.

In addition, as for an output of the semiconductor laser, since measurement sensitivity improves in proportion to the output, it is desirable that it is as high as possible. Therefore, what is necessary is just to select wavelength to which an absorbance becomes as high as possible in consideration of a molar extinction coefficient of water, a molar extinction coefficient of a measuring object, and an output of a semiconductor laser.

In addition, generally, a semiconductor laser is classified into an index guided type or a gain guided type. An index guided type semiconductor laser has characteristics such as a single spectrum in comparison with a gain guided type, usually small output variation, and astigmatism of 10 μm or less. In application to a thermal lens spectrometry, since the above-described three characteristics influence an S/N ratio (Signal-to-Noise ratio) of a thermal lens signal, it is desirable to use an index guided type.

On the other hand, as for a semiconductor laser used as probe light, what is necessary is that wavelength differs from the wavelength of the excitation light, and an output is acceptable so long as the detection means 18 to be used can fully detect it. However, as for wavelength, it is more desirable that absorption by the measuring object is small and absorption by other impurities is small. In addition, when a sample has photolysis property, it is desirable to use a semiconductor laser with the wavelength nearer to a infrared region. As for a waveguide type, an index guided type semiconductor laser is desirable like the case of the excitation light.

In addition, as another types of semiconductor lasers, since a distributed feed back (DFB) type and a distributed Bragg reflector (DBR) type which are made by engraving a diffraction grating in each resonator can narrow spectral band width and can stabilize wavelength, they are desirable.

Furthermore, as semiconductor lasers which can be used, it is possible to use a laser where beam geometry of outgoing light is made to be a perfect circle by incorporating an optical system for the formation of a perfect circle (for example, a micro lens) into a semiconductor laser device itself although outgoing light is still divergent light, or it is also good to use outgoing light from an optical fiber by connecting the optical fiber to a semiconductor laser. In these cases, although it becomes unnecessary to separately provide means for forming a perfect circle, it still be very effective means to bring outgoing light close to collimated light by using a collimator lens, and to adjust a focal point by a condenser lens since the outgoing light is divergent light.

Similarly, since there is a light emitting diode (LED) as small and inexpensive light-emitting means, it is also good to use an LED equipped with the required output instead of a semiconductor laser. Furthermore, if outgoing light from LED is separated into spectrum by certain means, it is possible to narrow spectrum just like a semiconductor laser, and if the wavelength to be separated into the spectrum is changed, it becomes possible to obtain the absorption spectrum of a measuring object within the range of the oscillation wavelength of the LED, which becomes more desirable.

In addition, although being expensive, a small solid state laser (for example, YAG laser etc.) can be used for either the excitation light or the probe light.

As a mechanism driving the semiconductor laser, any one of an output control type or a current control type is acceptable. However, since the output control type does not need the Peltier element described later, total cost is reduced by its part cost.

In the output control type, since it acts as a direct monitor of an output from a semiconductor laser to regulate its signal level, the output does not change even if a temperature change happens by laser oscillation, and hence, the influence on a measurement becomes small. This is because the output of the semiconductor laser can be controlled directly by a drive voltage, and, unlike a gas laser, its stability can be made to 1% or less.

Owing to such characteristics, a semiconductor laser can obtain 1% or less of output stability within 1 minute after start-up. In addition, similarly, also in an on-site analysis, although it is easily expected that a temperature change by the convection of air etc. happens, an output can be kept constant also in that case, and hence, output controllability is also a very important characteristic in POC analysis etc.

In the current control type, although a drive current is set constant, its output is influenced by a temperature change. In this case, the output can be stabilized if the temperature of the semiconductor laser beam-emitting apparatus is lowered by a Peltier element etc. to keep constant temperature. Furthermore, it becomes possible to prolong the life of a semiconductor laser and a frequency of apparatus maintenance may be fewer, which is desirable. Furthermore, the fluctuation of the semiconductor laser beam in the axial direction by a temperature change inside a resonator can be reduced and the noise in the above-described detection means 18 can be reduced by such temperature control, which becomes still more desirable.

It is preferable that an electric modulation mechanism is provided in an excitation light controller for excitation light to be able to be modulated electrically. Thus, if the output of the excitation light can be modulated according to the electric modulation mechanism, this becomes a periodic repeat signal, and hence it becomes possible to perform integrationetc. in signal extraction, and the above-described S/N ratio can be improved. In addition, since this enables the use of synchronous detection means such as a lock-in amplifier for signal extraction, the further highly accuracy is realizable.

Furthermore, if this modulation is enabled to about 100 MHz, a modulation frequency for a thermal lens is usually about 10 kHz in the maximum and frequency bands differ 10000 times, and hence, it become possible to superimpose two frequency simultaneously without being influenced by this high frequency. Therefore, while thermal lens measurement is attained, the increase of noise by return light is reduced.

In addition, since a rare gas laser such as He—Ne laser cannot perform electric modulation, it is necessary to newly provide mechanical modulation means such as a chopper into an optical path of the excitation light. In this case, since vibration originating in the rotation of the chopper arises and it becomes noise, it may become a factor which further disturbs the miniaturization of an apparatus, and cost reduction.

(With Respect to Focusing Optical System)

As mentioned above, in a thermal lens spectrometry, focusing excitation light to an optimal range, and making a focal point of probe light differ from a focal point of excitation light are important points for realizing a high S/N ratio.

The outgoing light of a semiconductor laser is divergent light, and its divergence angle is different according to the cross sectional direction of abeam. Furthermore, since there is astigmatism that a focal point differs according to the cross-sectional direction of a beam even if the above-described outgoing light is focused by a lens, it is necessary to correct it when being incident on a thermal lens. Since it becomes possible by this correction to uniquely specify beam diameter and a focal point without depending on cross-sectional geometry, this is desirable because of easy optimization of the beam diameter and focal point. In addition, even if a beam just after out-going from semiconductor laser beam-emitting means is focused in a sample with a lens as it is, focusing to the beam diameter of 10 μm or less is impossible.

Then, it is desirable to collimate excitation light by the collimator lens 11 for excitation light. Owing to this, the outgoing light that is divergent light is collimated to be made collimated light. As for the collimator lens 11 for excitation light, a single lens may be used, or a combination lens is sufficient so long as it has positive focal length, or a GRIN lens with refractive index distribution maybe used. Preferably, it is desirable to use the combination lens whose aberration is corrected since it can suppress the aberration to the minimum and can keep beam characteristics good. In addition, it is still more desirable that the aberration generated by the thickness of an outgoing window of a semiconductor laser is corrected. As for these lens characteristics, the collimator lens 21 for probe light is the same.

In addition, since semiconductor laser beam-emitting means is weak in return light by an optical system and a noise component becomes large since output variation etc. are produced by return light, it is desirable that both the collimator lenses 11 and 21 are given antireflection coating etc.

As mentioned above, when sharing a condenser lens between the excitation light and the probe light for making beam diameter small to some extent and focusing the beam to a sample, the simple adjustment means of a focal point of the probe light is to displace the collimator lens 21 for probe light from its collimate location to the direction of an optical axis.

In a conventional method, a focal point of the probe light was adjusted at a point where sensitivity becomes optimum by displacing a lens location in the direction of an optical axis by using separate condenser lenses for excitation light and probe light. However, in this case, since it is not possible to secure a space for making the excitation light and probe light coaxial when the focal length of each condenser lens is shortened in order to improve focusing property, there is a limitation in making the beam diameter in a focal point small.

In this embodiment, it is possible to realize the small beam diameter of the excitation light and the simple adjustment of a focal point of the probe light simultaneously with fewest number of parts. This becomes possible because the outgoing light of the semiconductor laser is divergent unlike a gas laser.

Thus, when the gas laser which is collimated light is used, a focal point cannot be adjusted even if the distance in the direction of an optical axis between the light source of the probe light, and the collimator lens 21 for probe light is changed. In addition, the collimator lens 21 for probe light can adjust a focal point of probe light, and can bring the outgoing light of a semiconductor laser close to collimated light and lead it to a condenser lens in optimal beam diameter, it becomes possible to simultaneously realize two important functions of increasing a degree of focusing of probe light and suppressing power loss, in the thermal lens spectrometry.

It is desirable to use a lens with longer focal length for the collimator lens 21 for probe light which most simply adjusts a focal point like this embodiment. If a lens with especially short focal length is used, it becomes possible to use large numerical aperture, and can bring a beam close to collimated light with suppressing the power loss in the collimator lens 21 for probe light to the minimum. However, in using a semiconductor laser as probe light, a collimated beam becomes an ellipse determined by a ratio of divergent angles in the cross sectional directions, and if it is focused while it is elliptic, the beam waist in a focal plane, i.e., a focus takes on different values according as the cross sectional direction.

The optimal difference of focal point of excitation light and probe light which are known in well-known technology depends on this beam waist (Thierry Berthoud et al., Anal. Chem., Vol. 57, 1216–1219, 1985). However, about the optimal value, since it is dependent on various other parameters and is complicated, each theoretical formula proposed up to now is not perfect, and hence, forecast is impossible. Therefore, it is necessary to determine an optimal value experimentally according to a system.

Since the optimal difference of the focal points differs when the beam waist changes according to the cross sectional direction as described above, it is difficult to set an optimal value for both directions. In this case, it is necessary to correct the collimated beam, which is elliptic, by providing the means, which enlarges the beam in only one direction, such as a prism, immediately after a collimator lens. In addition, the optimal difference of focal points changes also with the value of the astigmatism of a semiconductor laser.

When a focal length is long to some extent, a stray arises in the collimator lens 21 for probe light, and it causes power loss. However, since its outgoing light has a profile near a perfect circle rather than an ellipse and a degree that a value of beam waist also differs according to the cross sectional direction becomes small, it becomes easy to set the difference of focal points optimal. Also in this case, a simplest and low-cost method as means of adjusting a focal point is to displace the collimator lens for probe light in the direction of an optical axis from a collimating location.

In this embodiment, although a common condenser lens 15 for focusing is installed unlike conventional technology in order to focus a beam and to improve sensitivity, it is possible to adjust a focal point simply and continuously according to necessity, by displacing the location of the collimator lens 21 for probe light in this case. Since it is not necessary to change in particular the characteristics of a lens even when a divergent angle varies with the lot of a light-emitting apparatus like a semiconductor laser, this is very effective. In addition, when astigmatism is very large like a gain guided type semiconductor laser, an optical system (cylindrical lens etc.) which corrects the astigmatism may be provided in front of or behind this collimator lens 21.

Next, when optical path length is further short like an analysis in μ-TAS, an optical system for making a beam of excitation light smaller is further needed.

First, since the sensitivity of a thermal lens signal is proportional to the intensity of excitation light, it is necessary to design an optical system so that power loss may be suppressed as much as possible. Therefore, the collimator lens 11 for excitation light with much long focal length cannot use. In addition, if it is shortened too much, an incident angle to the prism 12 which enlarges a beam in only one direction become large and reflection loss at the place becomes large nonlinearly at Brewster's angle or more as derived from a Fresnel equations, and hence, it is necessary to determine a focal length in consideration of this reflection loss and loss by the stray at the collimator lens 11 for excitation light.

In particular, these losses become more remarkable when the major axis of an ellipse and the polarization direction of a semiconductor laser beam in a far-field (point which is separated from an exit aperture of a semiconductor laser by 50 cm or more) of the outgoing light of a semiconductor laser coincide. In this case, when two prisms 12 are prepared and are used as a prism with facing each other for inclined faces, it is possible to lessen an incident angle to each prism 12 with fixing a magnification, and hence, it is desirable since the power loss of the excitation light by reflection loss can be suppressed. The incident angle to the prism 12 may be set at an angle at which the major axis and minor axis of an ellipse determined by the focal length of the collimator lens 11 for excitation light become equal to each other.

The beam splitter 14 is required in order to lead the excitation light and probe light to the condenser lens 15 coaxially, and it is desirable that its reflectance for excitation light is close to 100%. In addition, it is desirable that a transmittance ratio for probe light is a transmittance ratio at which required sensitivity can be obtained in the detection means 18.

In addition, as for the condenser lens 15, it is desirable for lessening power loss that its pupil diameter is nearly equal to the beam diameter of the excitation light just before incidence. As for the condenser lens 15, although it can be made of a lens which consists of a single lens or two or more lenses, it is desirable that it is an aberration correcting lens.

In addition, a cylindrical lens 13 is used as correction means when the astigmatism of excitation light is large, and is installed immediately after the prism 12. Furthermore, it can be installed after the collimator lens 11 for excitation light.

Such an optical system for tightly focusing a beam smaller enables the enhancement of alignment accuracy when performing the alignment automatically by using the light reflected from the sample cell 16 which consists of glass, a resin, or the like, and is effective for measurement automation.

(With Respect to Light-receiving Optical System)

Light-receiving optical system has rolls of cutting the excitation light transmitting or being reflected from a sample, and leading the center of the probe light similarly transmitting or being reflected from the sample to the detection means 18. In addition, this embodiment is the case where the transmitted light is used.

In this embodiment, although a filter 19 is used for the cut of the excitation light, a spectrometer or the like can be used. In addition, since the filter 19 with higher optical density is better, it is desirable that it is five or more.

In addition, although a pinhole 17 is adopted as an article of making only a core part of the probe light, transmitting or being reflected, transmit, it is also good to lead only the center part of the probe light to the detection means 18 without using the pinhole 17.

Up to now, the necessary distance from the sample 16 to the pinhole 17 is usually about 1 m. Namely, if the pinhole 17 is not installed in a location which is apart by 1 m or more from a thermal lens which is not shown but exists in the sample 16, a change in light intensity of the probe light by a thermal lens effect becomes small, and in consequence, the sensitivity of a thermal lens signal falls.

This becomes an obstacle for the miniaturization of the whole optical system including the light-receiving optical system. In addition, if an optical path is lengthened as described above, pointing noise by the fluctuation of laser light in the direction of an optical axis become large, and hence, this become a cause of lowering the S/N of measurement.

In this embodiment, since the focusing degree of a condenser lens is increased for the improvement of sensitivity and a degree of focusing of probe light is also improved in connection with it, it is possible to shorten the distance from a sample to a pinhole.

The beam diameter of probe light in conventional technology was about 200 $\mu$m at the minimum, and the necessary distance from a sample to a pinhole was at least about 1 m. However, in this embodiment, as shown in the following example, when the beam diameter of the probe light was 9 $\mu$m, the distance from the sample to the pinhole was 2 cm, and the sensitivity of an absorbance was higher by one figure than that in conventional technology.

Therefore, it can be seen that, when the beam diameter increases to about 20 times, the distance from the sample to the pinhole becomes 50 times. If this distance is allowed to be up to 10 cm, what is necessary is to perform proportion simply and to make the beam diameter of the probe light up to about 50 $\mu$m. In addition, in order to shorten the above-described distance more than this, what is necessary is just to further focus the probe light, and it can be made to 0.2 $\mu$m theoretically.

In this embodiment, since an optical system including a light-receiving optical system is integrated into a unit by using a semiconductor laser and simple focal point adjustment means for probe light is also provided, what limits its size is the size of component parts themselves in the optical system from a light source to a condenser lens, and hence, shortening the distance between a sample and a pinhole leads to the miniaturization of the optical system as it is.

Although the above is the case where detection is performed by using the transmitted light from a sample, it is also possible to shorten the distance from a sample to a pinhole in the case of using the reflected light from the sample, similarly. In case of using the reflected light, what is necessary is just to attach a certain reflective film to the sample cell 16, or to provide a mirror after the sample cell 16. In case of directly attaching a reflective film to the sample cell 16, the intensity of the reflected light from this film becomes large as described later. Therefore, by using this reflected light, this is desirable since it becomes easy to perform optical auto-focusing as described later. However, in the case that this reflective film absorbs the above-described excitation light with exceeding 1%, a true signal is affected by this as a background signal, and hence, it is desirable to use a low absorptive material with 1% or less of absorptance.

In addition, since it is likely to cancel a thermal lens effect before and after reflection if a focal point of the probe light is further from a condenser lens 15 than a focal point of the excitation light when using the reflected light, it is desirable that the focal point of the probe light is closer to the condenser lens 15 than the focal point of the excitation light.

A photodiode or the like which has sensitivity to the wavelength of the probe light is used as the detection means 18. If necessary, it is also good to provide an amplifier with low noise in the detection means 18, and, to finally amplify an electric signal to required amplitude.

(With Respect to Sample Cell and Sample)

As for the sample cell 16 for installing a sample, it is fundamentally no problem that its cross sectional geometry is any geometry. It is desirable that a surface into which a light comes and through which the light is transmitted may be flat. Other faces may have rectangular cross-sections whose depth (optical path length) only is shallow but whose width is wide, or a thin glass capillary with 10 $\mu$m to hundreds $\mu$m of width, a micro channel made by processing a microchip with ultra-fine processing technology, or the like is also sufficient. In addition, it is desirable that the depth of a sample cell is 1000 $\mu$m or less so that the amount of a used solution may become minimum.

In addition, although it is possible to use it without a specific problem so long as it is optically transparent material as the material of the sample cell 16, it is desirable to use a low absorptive material with 1% or less of absorptance since a true signal is affected by it as a background signal when absorbing the excitation light by exceeding 1%. For example, transparent resins such as an acrylic resin, a polycarbonate resin, and a polystyrene resin are cited. It is possible to produce a microchannel etc. by injection molding, compression molding, etc. by using these resins.

A sample which is a measuring object is not especially limited so long as it absorbs the wavelength (for example, 635 nm) of the excitation light. So long as a signal processing method for extracting a component having the same period as a modulation frequency of the excitation light such as a lock-in amplifier detection is adopted even if the wavelength (for example, 780 nm) of the probe light is absorbed, the influence which the absorption of the probe light by the sample gives to a thermal lens signal is small.

In particular, in case of applying a semiconductor laser to a double beam method like this embodiment, a mechanical modulation mechanism which needs processing and rotation accuracy is unnecessary, and hence, it is possible to inexpensively modulate the excitation light by a current. Usually, since the overshoot and vibration which originate in the relaxation oscillation of excitation electrons in a resonator of the semiconductor laser at a leading edge or a trailing edge of its waveform are observed if the excitation light is modulated, remarkable influence is given to a thermal lens signal since the change of this waveform is added to a waveform change by a thermal lens effect in the case of a single beam method of detecting the excitation light as it is.

However, in the case of the double beam method like this embodiment, in addition to the detection of the probe light, instead of the excitation light which is modulation light, the time of the above-described relaxation oscillation is dozens ns, which is very short in comparison with several ms to hundreds ms of leading time constant of the thermal lens and is negligible, and hence, the modulation of the excitation light can become inexpensive and simple modulation means with hardly affecting the thermal lens signal.

On the other hand, when the sample consists of many components and substances except objective substance absorb the wavelength of the excitation light, it is difficult to extract a thermal lens signal that is unique to the objective substances. However, also in this case, as shown in measurement in impurities such as a blood test, if only the objective substance can be made to uniquely color by using an enzyme reaction, it is satisfactory. As such an example, there is a reaction system of the enzyme reaction or coloring of cholesterol measurement in blood, and it is possible to quantitatively measure the concentration of cholesterol by the thermal lens spectrometry by using a kit such as cholesterol E-HA test Wako (made by Wako Pure Chemical Industries, Ltd.) or the like.

In addition, since plenty of reaction systems which specifically react only to objective substances by enzyme reactions or complex forming reactions besides this example, and make them finally color are known, it is possible to perform measurement in blood or environmental water, where many impurities exist, or the like in sufficient accuracy by using these.

(With Respect to Alignment Procedure)

Up to now, a microscope has been used for alignment when a degree of focusing of a condenser lens has been improved. That is, a location of a sample cell was adjusted at an optimal location for measuring a thermal lens signal by visually adjusting the positional relation of the sample cell and a focal point of a beam by using the microscope.

However, as for usual microscopes, since the size of even a small one was 15 cm D×15 cm W×30 cm H, an optical system became large-sized, and the adjustment of a location of the sample cell was manual adjustment with eyes, and hence this has become an obstacle in realization of high accuracy and automation of a photothermal spectroscopic analyzer.

In this embodiment, since a location of a sample cell is optically detected and is quantified by using the reflected light from the sample cell, a microscope became entirely unnecessary and sharp improvement is performed also in respect of miniaturization.

As the above-described optical detection method, it is possible to cite, for example, an astigmatic method of dividing light, reflected from a sample cell, by a beam splitter, further letting it pass through a cylindrical lens, recognizing the cross sectional geometry of the above-described reflected light with a quadrant photodiode, and determining the positional relation of a sample cell and a focal point. Although such an astigmatic method is desirable since the sensitivity of detection of a focal point is high, a method of optically detecting a location of a sample cell is not limited to the astigmatic method, but a critical angle method or a knife edge method is also sufficient if sensitivity required is obtained.

Since it is possible to highly accurately detect a boundary between glass and air and a boundary between glass and a sample when a glass sample cell is used by using such a focus servo, it is possible to align a focal point with an arbitrary point with high accuracy by utilizing the result and using a stage etc.

In particular, in this embodiment, since it is possible to share a condenser lens between the excitation light and probe light and to greatly make a beam small, it becomes possible to perform alignment with precision equivalent to a micrometer became possible by the above-described focus servo.

In addition, as described above, when using a reflective optical system for a light-receiving optical system, it is possible to share the light-receiving optical system and autofocus optical system by detecting a change in a focal point by the thermal lens effect by using not only a detection method with a pinhole but also the above-described servo which determines a focus position, and hence, it is also possible to obtain a simplified optical system.

In addition, since the excitation light has short wavelength and is incident on an objective lens in cllimated light if the excitation light is used for such an alignment, beam diameter in a focal point becomes small, and hence, alignment with high accuracy becomes possible. In addition, it is possible to adjust a focal point highly accurately and automatically also in the direction of groove width by using the same method when it is necessary to align a focal point in a thin groove in a microchip etc. and only changing a computing method of each quantity of light detected by a quadrant photodiode.

Next, the measurement using a photothermal spectroscopic analyzer according to the present invention will be described in detail with referring to drawings.

EXAMPLE 1

An example where optics are separately fixed on an optical bench, a microscope is used, and both the light sources of excitation light and probe light are made of semiconductor laser beam-emitting apparatuses will be described in detail.

Figure 2:
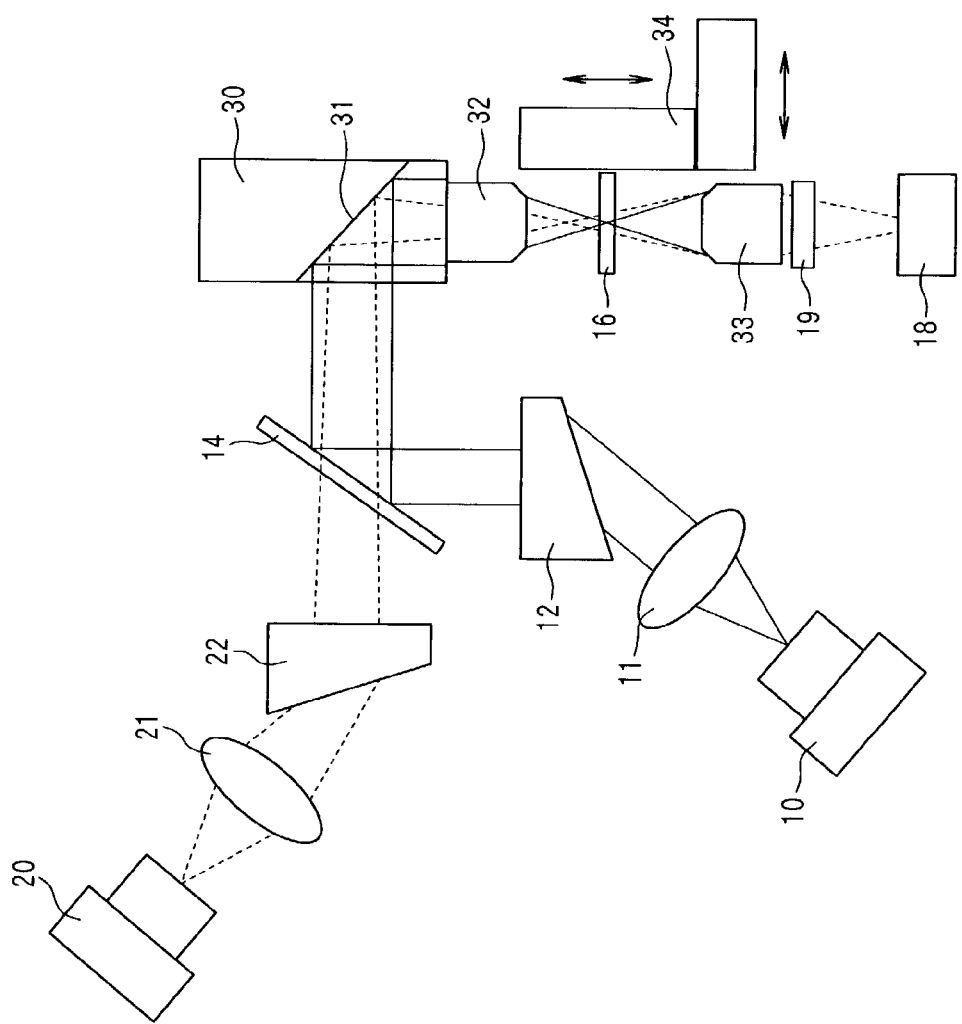
FIG. 2 is a structural diagram explaining a construction of the photothermal spectroscopic analyzer according to the example 1.

FIG. 2 is a structural diagram explaining a construction of a photothermal spectroscopic analyzer used in this example. In addition, since the construction of a photothermal spectroscopic analyzer in FIG. 2 is almost the same as the construction of the photothermal spectroscopic analyzer in FIG. 1, only different portions will be described and the explanation of the same portions will be omitted. In addition, in FIG. 2, the same symbols in FIG. 1 are assigned to the portions identical or equivalent to those in FIG. 1.

A semiconductor laser beam-emitting apparatus with the wavelength of 635 nm and a rated output of 20 mW (DL-4038-025 made by SANYO Electric Co., Ltd.) was used for a light source 10 of excitation light. A constant current control driver (TC-05 visible light type DPST2001, Japan Science Engineering Co., Ltd.) equipped with a Peltier element which can perform temperature control of a semiconductor laser device at about 25° C. was used in a drive circuit of this apparatus. In addition, since this driver is equipped with a modulation function, it is possible to modulate an output at an arbitrary frequency by inputting a modulation signal from the external device. A function generator (8116A, made by Hewlett-Packard Co.) was used for such a modulation signal generator.

In addition, a semiconductor laser beam-emitting apparatus with the wavelength of 780 nm and a rated output of 15 mW (DL-4034-151, SANYO Electric Co., Ltd. make) was used for the light source 20 of probe light. A constant current control driver (TC-05 infra-red type DPST2001, made by Japan Science Engineering Co., Ltd.) equipped with a peltier element which can perform temperature control of a semiconductor laser device at about 25° C. was used in a drive circuit of this apparatus.

Furthermore, a collimating lens for a laser diode with the focal length f of 14.5 mm and the numerical aperture of 0.276 (06GLC003, made by Melles Griot Inc.) was used for the collimator lens 11 for excitation light. Then, the same lens as is described above was also used for the collimator lens 21 for probe light. Translation stages (07TAC504, made by Melles Griot Inc.) which are not shown were provided in mounts of both of these collimator lenses 11 and 21 to make it possible to displace them in the resolution equivalent to a micro meter in the direction of an optical axis.

Furthermore, no-mount prisms for a pair of anamorphic prisms (06GPU001, made by Melles Griot Inc.) were used for the prism 12 for excitation light and the prism 22 for probe light.

Moreover, a wavelength dependent beam splitter for a laser diode (03BDL003, made by Melles Griot Inc.) was used for the beam splitter 14. Since having a reflective band of 550 to 650 nm, and a transparency band of 760 to 1600 nm, this can reflect or transmit the excitation light (635 nm) and probe light (780 nm), which were used for the photothermal spectroscopic analyzer of this example, by about 100%.

Furthermore, a tool microscope equipped with the half mirror 31 (XR1004, made by Carton Optical Industries, Ltd.) was used for the microscope 30 so that the excitation light and probe light which were made coaxial could be introduced from its side. In addition, an antireflection coating that acts at 635 nm and 780 nm is applied to the half mirror 31. An achromat objective lens with the numerical aperture of 0.4 (M955-40, made by Carton Optical Industries, Ltd.) was used for the objective lens 32 of the microscope 30. This objective lens 32 plays the role of a condenser lens (condenser lens 15 in FIG. 1) which focuses excitation light in a sample and focuses probe light in the above-described thermal lens. In addition, a similar lens was used for the objective lens 33 for light-receiving.

Furthermore, a laser line interference filter (03FIL056, made by Melles Griot Inc.) with the central wavelength of 780 nm and the half width of 20 nm was used for the filter 19 which cuts the excitation light.

Moreover, a silicon PIN photodiode (DET110, made by THORLABS Inc.) was used for the detection means 18. An output from this detection means 18 is a voltage output by a 50-Ω terminator (T4119, made by THORLABS Inc.) which is not shown. A low noise preamplifier with the gain of 100 (LI-75A, made by NF Circuit Block Corporation) was used for voltage amplification (not shown). Then, a two-phase lock-in amplifier (5610, made by NF Circuit Block Corporation) was used for a thermal lens signal detector (not shown).

An output of this lock-in amplifier was connected to a connector (CB-50LP, made by National Instruments Corporation) through a BNC cable, and an output from the connector was fetched into a notebook computer with a data acquisition card (DAQCARD-700, made by National Instruments Corporation). A signal fetched into the notebook computer was displayed on a display unit of the above-described notebook computer by software (Labview 5.0, made by National Instruments Corporation), and was saved in a recording device of the above-described notebook computer. In addition, in order to measure the beam diameter, coordinates of a center, an inclination angle of a major axis of an ellipse, an output, and those time-dependent changes of a laser beam, a beam analyzer (Beam Alyzer 13SKP001-SA, made by Melles Griot Inc.) which was not shown was used.

Furthermore, an automatic positioning stage (MINI-60X MINI-5P, made by SIGMA KOKI CO., LTD.) which can position two axes in the direction of an optical axis and the direction perpendicular to the optical axis in a 1-micrometer level of resolution was used for the stage 34 on which the sample cell 16 was placed.

Next, methods from the adjustment of an optical system to measurement of a thermal lens signal in the above-described photothermal spectroscopic analyzer will be described.

At the time of adjusting the optical system, first of all, the probe light is adjusted. With looking at the analysis result of the beam by the above-described beam analyzer, the light source 20 of the probe light is mounted so that the major axis of an ellipse of outgoing light may become perpendicular to the top face of a surface plate on which the optical system is fixed. Next, the optical axis of the collimator lens 21 for probe light is adjusted. Thus, beam diameter in a point near the collimator lens 21 for probe light and a point apart by about 1 m is measured with the above-described beam analyzer, distance between the light source 20 of the probe light and the collimator lens 21 for probe light is adjusted so that they may become equal, and the location is determined to become collimated light (reference location). The collimator lens 21 for probe light was adjusted at a location which becomes optimal for thermal lens measurement by displacing the collimator lens 21 for probe light from the reference location by fixed distance. The focal point of the probe light is uniquely determined by the amount of displacement from the reference location.

Next, the prism 22 is installed as shown in FIG. 2, and is rotated on a rotation stage etc. until the minor axis of an ellipse of the above-described outgoing light becomes coaxial with the major axis, and an incident angle is adjusted. After letting the outgoing light from prism 22 pass through the beam splitter 14, the microscope 30 is installed and the probe light is incident on the objective lens 32 of the microscope 30. Furthermore, in order to receive the transmitted light from the sample which was placed in the sample cell 16, the objective lens 33 for light-receiving is installed, an axis of this objective lens 33 is aligned with the optical axis, and it is adjusted so that the outgoing light may become collimated light.

Then, the filter 19 is arranged between the objective lens 33 for light-receiving, and the detection means 18. In addition, although a pinhole could be established between the filter 19 and detection means 18 as shown in FIG. 1, in this example, the pinhole was substituted by shifting the objective lens 33 for light-receiving from a location, where collimated light was obtained, in the direction of the optical axis to make it stray in the condenser lens 33. At this time, the distance between the sample cell 16 and the objective lens 33 that was an alternative of the pinhole was about 2 cm.

After the adjustment of the probe light finishes, the installation of the light source 10 of the excitation light and the adjustment of the collimator lens 11 for excitation light and the prism 12 are performed by the same method.

Then, the excitation light and probe light are made to be coaxial by such adjustment at two points that the optical axis of the excitation and probe light is aligned on the beam splitter 14, and optical axes of both light are aligned at a location distant enough from the beam splitter 14 after adjusting the swing and tilt of the beam splitter 14. When axes coincide at two points, the excitation light is also perpendicularly incident on a pupil of the objective lens 32. It is good to install a swing and tilt mirror in a suitable place to make the above adjustment still easier. In addition, the optical path length from the light source 10 of the excitation light and the light source 20 of the probe light to the sample cell 16 is about 50 cm.

An analysis was performed by using such a photothermal spectroscopic analyzer, using a glass cell (AB20, made by GL Sciences, Inc.) with the optical path length of 50 μm as the sample cell 16, and using a xylene cyanol aqueous solution as the sample.

On the occasion of measurement, the sample cell 16 where the sample is installed first is put on the stage 34. Then, a location of the sample cell 16 is adjusted so that the excitation light and probe light may be incident on a measured portion. Furthermore, a focal point (depth location) of the excitation light is adjusted. In that time, it is good to adjust the focal point by using a microscope etc., while displacing the sample cell 16 by moving the stage 34. When the focal point exactly coincides with a boundary between air and glass, or a boundary between glass and the sample, the sample cell 16 is displaced by using the stage 34 on the basis of a bright spot since its reflected light is clearly observed as the bright spot under the microscope. In this way, after positioning the focal point at a predetermined depth location, measurement is performed by the thermal lens spectrometry.

Figure 3:
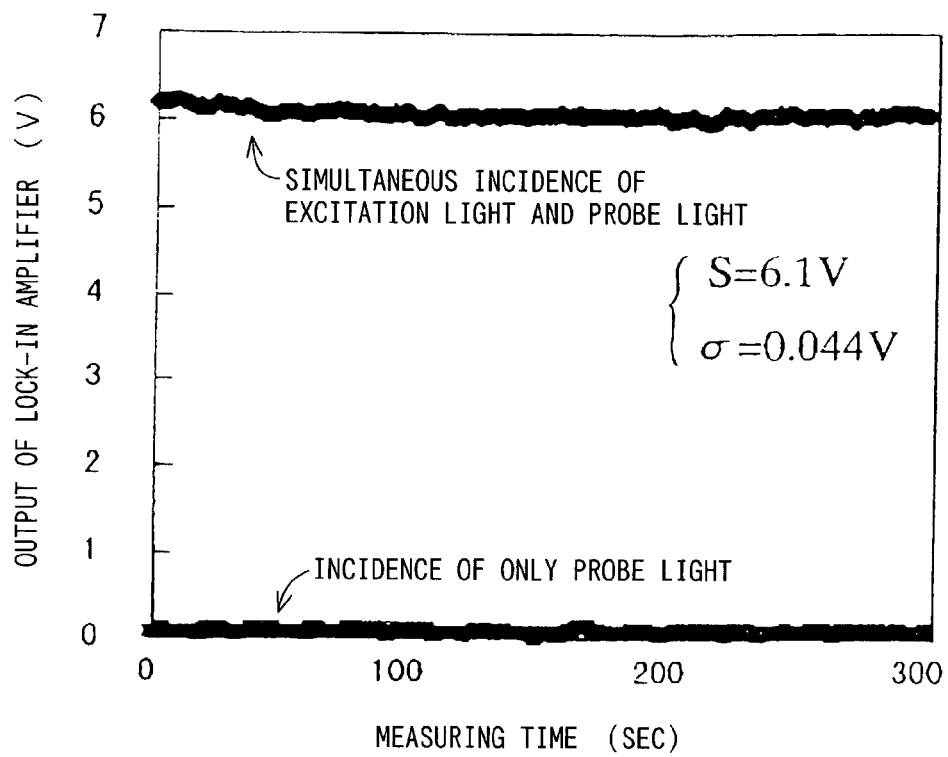
FIG. 3 is a chart showing a measurement result of a thermal lens signal in a xylene cyanol aqueous solution.

FIG. 3 shows the result of measuring the time-dependent change of a thermal lens signal in a xylene cyanol aqueous solution with the concentration of 25 μM. Measurement was performed for 5 minutes at intervals of 1 second. The modulation frequency was set at 2.1 kHz and the time constant of the lock-in amplifier was 1 sec. In addition, both the beam diameters of the excitation light and probe light at this time were about 9 μm.

As apparent from a chart in FIG. 3, although an output from the lock-in amplifier was 0.07 V on average when only the probe light was incident, and on the contrary, an output was about 6 V when the thermal lens was made to be formed by incidence of the excitation light. Since the standard deviation σ of the measurement for these 5 minutes is 0.044 V, CV (Coefficient of Variance) of the measurement at this time is about 0.7%, and hence, it can be seen that very stable measurement was performed.

Figure 4:
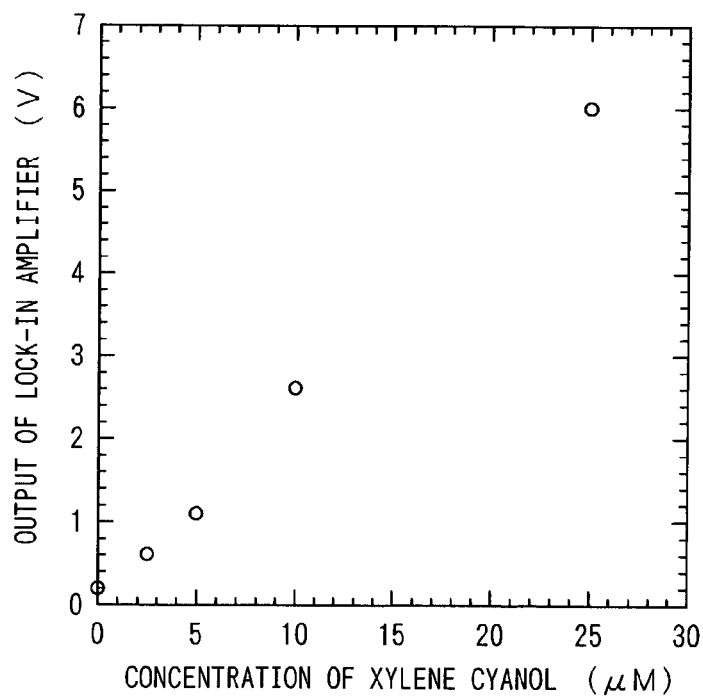
FIG. 4 is a graph showing a concentration dependency of a amplitude of a thermal lens signal on the xylene cyanol concentration in a xylene cyanol aqueous solution.

FIG. 4 shows a correlation between the amplitude of a thermal lens signal and the xylene cyanol concentration in the measurement of a thermal lens signal in a xylene cyanol aqueous solution. From this result, supposing detection limit concentration is the concentration at which S/N (Signal-to-Noise ratio) becomes 2, it was $3.6 \times 10^{-7}$ (mol/L). When the detection limit of absorbance in the photothermal spectroscopic analyzer of this example was found by multiplying it by a molar extinction coefficient of $3 \times 10^4$ (L/cm/mol) and the optical path length of $5.0 \times 10^{-3}$ (cm) of the xylene cyanol which were used in this example, it was about $5.4 \times 10^{-5}$ (Abs.) in the aqueous solution.

Figure 7:
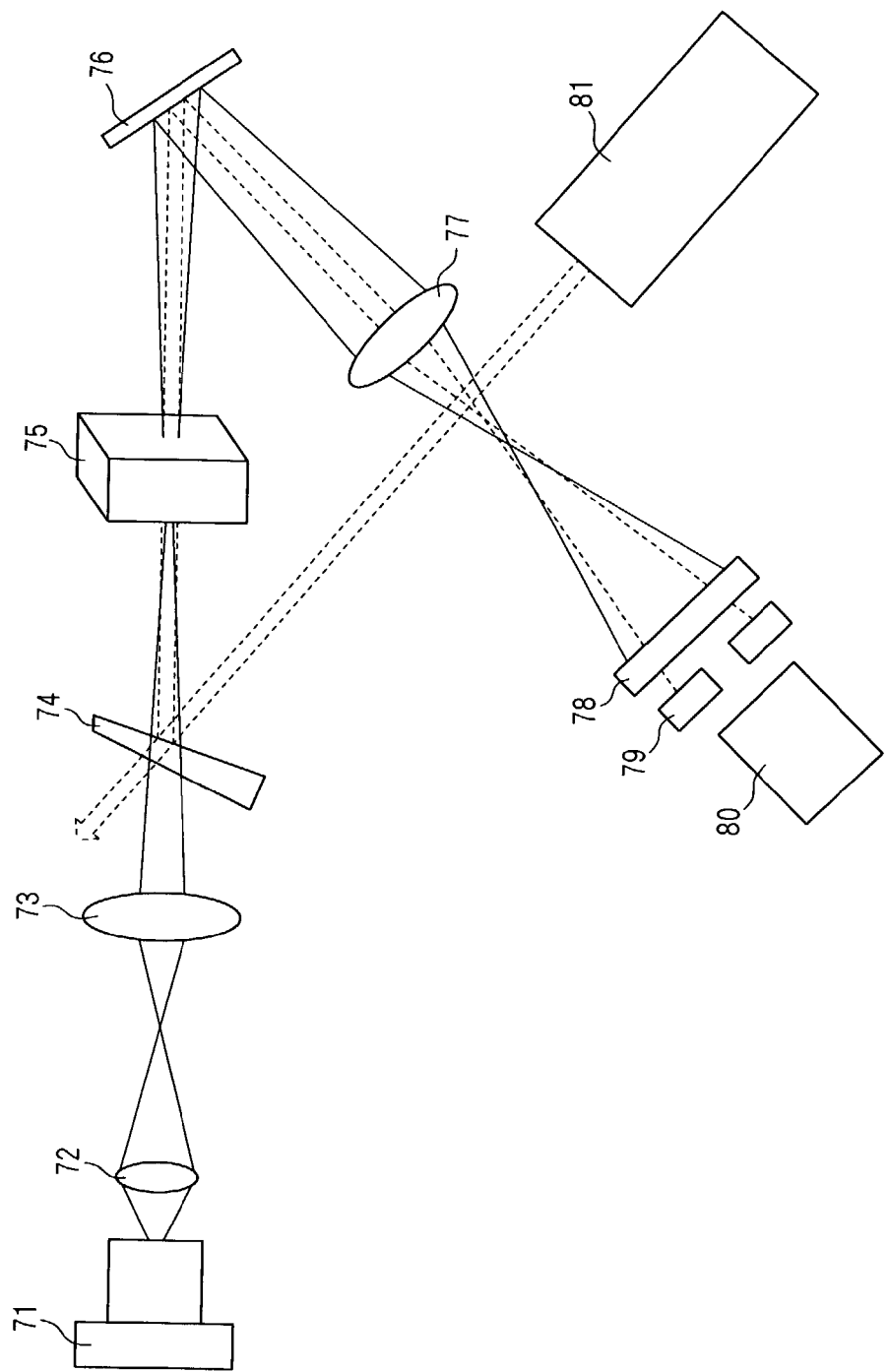
FIG. 7 is a structural diagram explaining a construction of a conventional photothermal spectroscopic analyzer.

Then, the detection limit of absorbance in the photothermal spectroscopic analyzer in FIG. 7 which is conventional technology was $2 \times 10^{-4}$ (Abs.), i.e., 0.2 ppb in the concentration of phosphorus, from the measurement where 2-butanol solution was used. However, since a detection limit is 0.7 ppb and a molar extinction coefficient in wavelength 823.9 nm becomes about ¾ times in comparison with the case of the 2-butanol solution when aqueous solution is used, the detection limit of absorbance in the aqueous solution is calculated to be $5.3 \times 10^{-4}$ (Abs.). Therefore, it can be seen that this example is ten times as high as conventional technology in sensitivity. In addition, in this example, the astigmatism was not completely corrected in both the excitation light and probe light, but about 40 μm remains.

In addition, in comparison with another conventional technology that a semiconductor laser light source is adopted as the excitation light similarly to the above, and the distance from a sample to a pinhole is shortened to 10 cm without contrivance (D. Rojas et al., Rev. Sci. Instrum., Vol.63, 2989–2993, 1992), this example is about 24 times as high as a conventional example in sensitivity (this conventional example is not shown).

As for the numerical aperture of a condenser lens, it is expected that there is a value at which sensitivity becomes optimal for the depth of a sample cell as mentioned above. Namely, since the conventional technology in FIG. 7 uses a sample cell with large depth that is 1 cm, it does not always lead to the enhancement of sensitivity to lessen the beam diameter of the excitation light to smaller size than 70 μm. However, in this example, since a semiconductor laser was used, beam diameters of the excitation light and probe light were set to 9 μm, and distance from a sample to a pinhole was shortened to 2 cm, it became possible to measure the minimum amount of sample in the sample cell with the depth of 50 μm with high sensitivity.

In addition, the adjustment of a focal point of the probe light is performed by a simple method of increasing focusing degree by sharing a condenser lens, adjusting the distance between the light source 20 of the probe light and the collimator lens 21 for probe light by displacing the collimator lens 21 for probe light without increasing a parts count. The measurement sensitivity is improved owing to this.

In addition, in this example, although both the distance between the light source 20 of the probe light and the collimator lens 21 for probe light and the distance between the light source 10 of the excitation light and the collimator lens 11 for excitation light were made adjustable, it is also good to make one of them adjustable.

EXAMPLE 2

Figure 5:
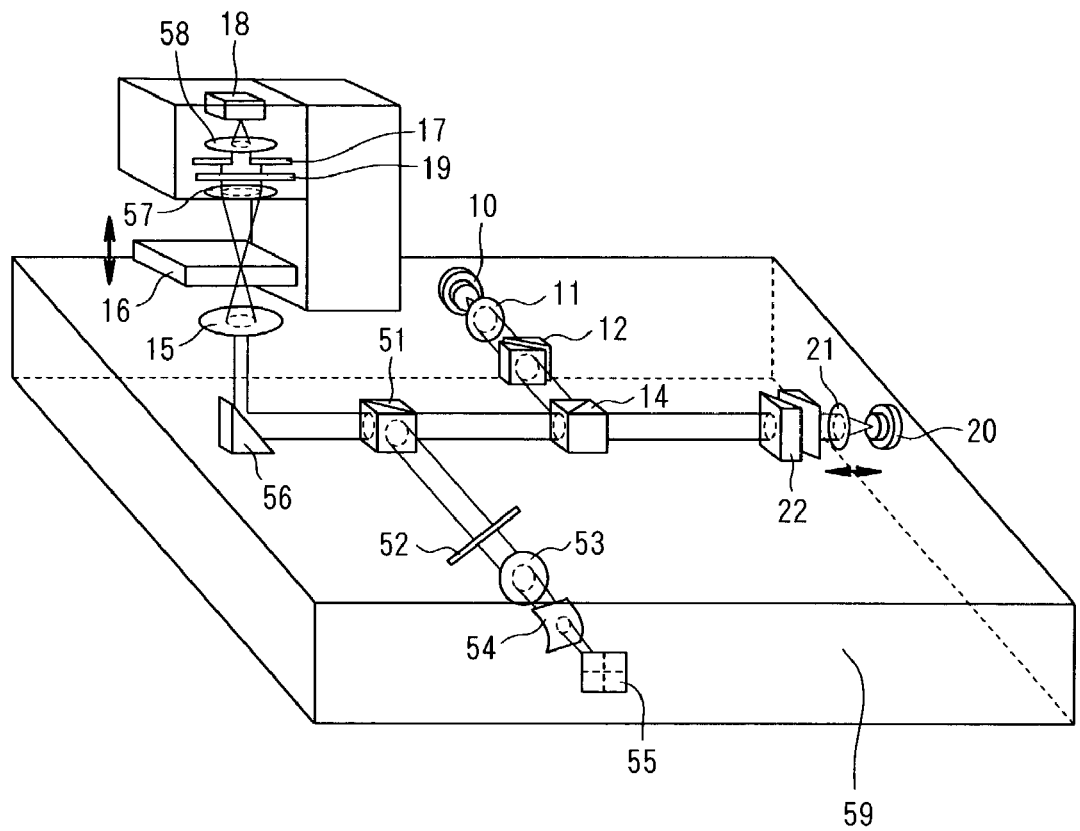
FIG. 5 is a structural diagram explaining a construction of a photothermal spectroscopic analyzer according to the example 2.

An example of which miniaturizing and integrating a portion from a light source to detection means will be described in detail with referring to FIG. 5. In addition, in FIG. 5, the same symbols in FIG. 1 are assigned to the portions identical or equivalent to those in FIG. 1. In addition, in this example, although several kinds of our own optics are used, it is natural to use commercial optics so long as they have the same characteristics.

A semiconductor laser beam-emitting apparatus with the wavelength of 635 nm and a rated output of 30 mW (LTO51PS, made by Sharp Corporation) was used for a light source 10 of excitation light. In addition, a semiconductor laser beam-emitting apparatus with the wavelength of 780 nm and a rated output of 50 mW (ML60114R, made by Mitsubishi Electric Corporation) was used for the light source 20 of probe light. These semiconductor lasers were made to enable output control and current control by commercial LD drivers (ALP-6323CA, made by Asahi data systems Ltd.) which are not shown.

LD drivers are connected to a personal computer through a PCI card (NIPCI-6025E, made by National Instruments Corporation) which is similarly not shown, and the personal computer can adjust the output, current, and modulation frequency of the semiconductor laser beam-emitting apparatus. In addition, a modulation frequency of the excitation light can be 0 to 100 kHz. Furthermore, both the excitation light and the probe light superimposed 350 MHz of high frequencies to suppress the influence by return light.

An own lens with the numerical aperture of 0.34 and the focal length of 8 mm was used for the collimator lens 11 for excitation light. An own lens with the numerical aperture of 0.39 and the focal length of 7 mm was used for the collimator lens 21 for probe light. The collimator lens 21 for probe light was attached on a micrometer head (MHT 3-5, made by Mitutoyo Corporation) which is not shown, and was made to be able to perform displacement in the direction of an optical axis in a micrometer level of resolution. In addition, a displacement method is not limited to this example.

Furthermore, an article made by making inclined planes of two own prisms face each other was used for the prism 12 for excitation light and the prism 22 for probe light. In addition, as for the prism 12 for excitation light, an angle between two prisms was adjusted so that a magnification might become 3 times. In addition, as for the prism 22 for probe light, an angle between two prisms was adjusted so that a magnification might become 2.6 times.

Furthermore, an own polarization dependent beam splitter whose transmittance to p-polarized light was 100%, and whose reflectance to s-polarized light was 100% was used for the beam splitter 14 for making the excitation light and probe light coaxial. In addition, in this case, since the excitation light is s-polarized light and the probe light is p-polarized light, power loss in this beam splitter 14 is about 0.

Furthermore, the numerical aperture of 0.4 and the focal length of 4.5 mm (350022, made by Geltech. Inc.) were selected for the condenser lens 15.

In addition, in order to lead the excitation light and probe light, which passed the beam splitter 14, to the condenser lens 15, a mirror prism 56 which makes both the above-described light refracted by 90° was used.

Next, a method of quantifying the positional relation between the sample cell 16 and the focal point of a laser beam by using the reflected light from the sample cell 16 will be described. In addition, in this example, although a method of quantifying the above-described positional relation by using an astigmatic method of detecting a location of the sample cell 16 with the cross section geometry of a beam of the reflected light was adopted, a method of quantifying the above-described positional relation is not especially limited, but a knife edge method or a critical angle method may be also used.

The reflected light from the sample cell 16 is led to an optical system for detecting a location of the sample cell 16 after being reflected by an own unpolarized light dependent beam splitter 51 whose transmittance and reflectances to the excitation light and probe light are set at 80% and 20% respectively. Only the probe light out of the reflection light of the excitation light and the probe light that are led to the optical system is cut by a laser line interference filter 52 with the central wavelength of 635 nm, and the half width of 10 nm (03FIL 250, made by Melles Griot Inc.), and is led to the condenser lens 53. An own lens with the focal length of 45.5 mm was used for the condenser lens 53.

An own cylindrical lens whose focal length in a curved surface is 286 mm was used for the cylindrical lens 54. The excitation light is focused by the condenser lens 53 and cylindrical lens 54 at the quadrant photodiode 55 (S6344, made by Hamamatsu Photonics K.K.), and light intensities in four photodiodes are converted into electric signals, respectively. These electric signals are led to a personal computer, which is not shown, through a PCI card (NIPCI-6025E, made by National Instruments Corporation) which is similarly not shown. Then, the relative distance between the sample cell and the focal point of the excitation light is quantified by performing data processing on the personal computer. In addition, in operation, the sum of outputs of two photodiodes located in opposing corners among four photodiodes of the quadrant photodiode 55 was calculated, and the difference of the two operation values was further calculated.

Next, an optical system of a light-receiving section will be described. In this example, although detection is performed by using the transmitted light, it is also good to perform detection by utilizing the reflected light by using a mirror or a reflective film as mentioned above.

In order to make into collimated light the excitation light and probe light which transmitted the sample, the same lens as the condenser lens 15 was used for the light-receiving lens 57. In addition, the numerical aperture of the light-receiving lens 57 is satisfactory so long as it is larger than the numerical aperture of the condenser lens 15. Furthermore, a laser line interference filter with the central wavelength of 780 nm and the half width of 20 nm (03FILO56, made by Melles Griot Inc.) was used for the filter 19 which cuts the excitation light.

Only a center part of the probe light transmitted the filter 19 was transmitted by the pinhole 17, was focused in the detection means 18 by the lens 58 (01LPX005, made by Melles Griot Inc.) whose focal length is 10 mm, and is converted into an electric signal. A quadrant photodiode (S6344, made by Hamamatsu Photonics K.K.) was used for the detection means 18. In this example, the sum of each electric signal of four photodiodes was calculated, and its signal was made to be an output from the detection means 18. In addition, it is not necessary to use a quadrant photodiode for the detection means 18, but a non-split photodiode is also satisfactory.

The output from the quadrant photodiode was converted into a voltage from a current by an own circuit. A conversion scale factor from a current to a voltage was set at 1000 times. In addition, a commercial circuit can be used as this conversion circuit from a current to a voltage so long as its conversion scale factor is 1000 times.

Furthermore, the converted voltage signal was led to a low noise preamplifier with the gain of 100 (LI-75A, made by NF Corporation) (not shown), and is further led to two-phase lock-in amplifier (5610B, made by NF Corporation) which is not shown. Then, only an electric signal which synchronizes with a modulation frequency of the excitation light was extracted, and it was made into thermal lens signal values (output of the lock-in amplifier).

An output of this lock-in amplifier was connected to a connector (CB-50LP, made by National Instruments Corporation) through a BNC cable, and an output from the connector was fetched into a notebook computer with a data acquisition card (DAQCARD-700, made by National Instruments Corporation). A thermal lens signal fetched into the notebook computer was displayed on a display screen of the above-described notebook computer by software (LAB-VIEW 5.0, made by National Instruments Corporation), and signal values and time-dependent changes of the signal values were saved (all are not shown).

Furthermore, an automatic positioning stage (MINI-60X MINI-5P, made by SIGMA KOKI CO., LTD.) which can perform alignment in the direction of an optical axis in a 1-micrometer level of resolution was used for a stage on which the sample cell 16 was placed and which is not shown.

The adjustment of an optical system was performed in the same procedure as the example 1, all the optics except the collimator lens 21 for probe light were fixed with adhesives on a box 59 made from aluminum after adjustment, and were integrated (unitized).

Next, measurement procedure of a sample will be described. A glass cell with the optical path length of 50 μm (AB20, made by GL Sciences, Inc.) was used as the sample cell 16, and this is placed on a stage, which is not shown, to be fixed. Then, the stage was moved in the direction of an optical axis, a boundary between air and glass was found with monitoring the operation result of outputs of the quadrant photodiode 55 by the personal computer which is not shown, and thermal lens measurement was performed at a location moved therefrom by certain length.

Figure 6:
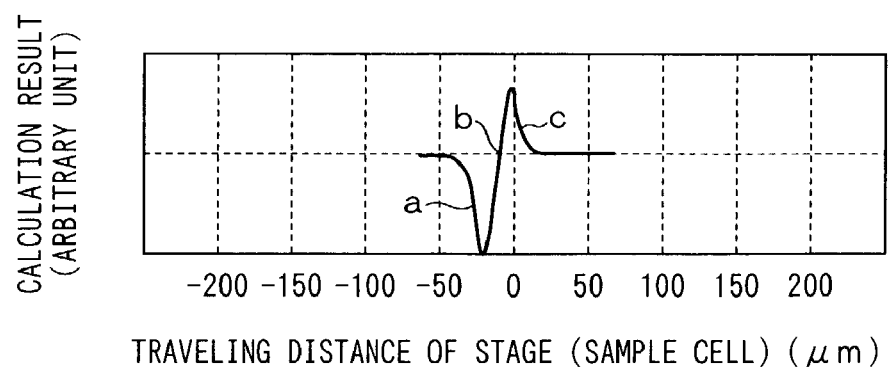
FIG. 6 is a chart showing an operation result of outputs of quadrant photodiode at the time of moving a location of a sample cell.

The operation result at the time of moving the stage in the depth direction is shown in FIG. 6. A region shown by symbol a in a graph in FIG. 6 shows that the sample cell 16 is far from a focal point of the excitation light by the condenser lens 15, and a region shown by symbol c shows conversely that they are too close. A point shown by symbol b which crosses a baseline shows that the boundary between air and glass and a focal point of the excitation light coincide completely.

The alignment accuracy of the sample cell 16 at this time determines the alignment accuracy at the time of finally aligning the sample cell 16 with the measuring point of the thermal lens. In this case, it was shown from the measurement result that the alignment in the accuracy of 2 μm or less was possible. Since a thermal lens signal changes about 2% if a location of the sample cell 16 shifts by 5 μm, in the POC analysis etc., where about 1% of accuracy is usually required, as seen from the result described later, it can be said that the photothermal spectroscopic analyzer of this example has alignment accuracy required for thermal lens measurement.

The measurement result of xylene cyanol by using the photothermal spectroscopic analyzer of this example will be described. The detection limit of an absorbance was $1.0 \times 10^{-5}$ (Abs.), and similarly to the example 1, the photothermal spectroscopic analyzer of this example was small and highly sensitive in comparison with conventional technology. In addition, in this example, the distance from a sample to a pinhole was 10 cm, and the size of the whole optical system was 15 cm D×15 cm W×15 cm H. Therefore, it is the size of being easily carried.

INDUSTRIAL APPLICABILITY

Thus, a photothermal spectroscopic analyzer of the present invention is equipped with all the requirements as an apparatus, performing a POC analysis etc., such as small size, inexpensiveness, high sensitivity, high accuracy, maintenance-free performance, short start-up time, and possibility of automatic measurement.

The invention claimed is:

1. A photothermal spectroscopic analyzer in which a probe light is incident on a thermal lens generated in a sample by incidence of an excitation light, and for analyzing the sample on the basis of a change in the probe light by the thermal lens in that case, comprising:
    a light source of the excitation light which comprises semiconductor laser beam-emitting means;
    a light source of the probe light which comprises another semiconductor laser beam-emitting means, wherein a condenser lens which focuses the excitation light in the sample and a condenser lens which focuses the probe light in the thermal lens are made to be a common lens;
    at least one detection means of detecting a change in the probe light by the thermal lens; and
    rounding means between at least the light source of the excitation light or the light source of the probe light, wherein the condenser lens brings the cross sectional geometry of at least one semiconductor laser beam emitted from the light sources into approximately the shape of a circle,
    wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

2. A photothermal spectroscopic analyzer in which a probe light is incident on a thermal lens generated in a sample by incidence of an excitation light, and for analyzing the sample on the basis of a change in the probe light by the thermal lens in that case, comprising:
    a light source of the excitation light which comprises semiconductor laser beam-emitting means;
    a light source of the probe light which comprises another semiconductor laser beam-emitting means, wherein a condenser lens which focuses the excitation light in the sample and a condenser lens which focuses the probe light in the thermal lens are made to be a common lens;
    at least one detection means of detecting a change in the probe light by the thermal lens; and
    astigmatism correction means between at least the light source of the excitation light or the light source of the probe light, wherein the condenser lens reduces the astigmatism of the semiconductor laser beam, emitted from the light source of the excitation light or the probe light,
    wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

3. A photothermal spectroscopic analyzer in which a probe light is incident on a thermal lens generated in a sample by incidence of an excitation light, and for analyzing the sample on the basis of a change in the probe light by the thermal lens in that case, comprising:

a light source of the excitation light which comprises semiconductor laser beam-emitting means;

a light source of the probe light which comprises another semiconductor laser beam-emitting means, wherein a condenser lens which focuses the excitation light in the sample and a condenser lens which focuses the probe light in the thermal lens are made to be a common lens;

at least one detection means of detecting a change in the probe light by the thermal lens;

at least one collimator lens where a semiconductor laser beam emitted from the light source of the excitation light is incident, or where a semiconductor laser beam emitted from the light source of the probe light is incident;

focal point adjustment means in the at least one collimator lens for adjusting a focal point of the semiconductor laser beam by changing a distance in the direction of an optical axis between the at least one collimator lens and the light source of the excitation light or the probe light;

means for adjusting a distance between at least one of focal points of the excitation light and the probe light; and a sample cell which contains the sample, wherein the adjusting means utilizes light reflected from the sample cells, wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm.

4. The photothermal spectroscopic analyzer according to claim 1, further comprising astigmatism correction means between at least the light source of the excitation light or the light source of the probe light, wherein the condenser lens reduces the astigmatism of at least one of the semiconductor laser beams emitted from the light sources.

5. The photothermal spectroscopic analyzer according to claim 1, wherein the light source of the excitation light and the light source of the probe light are semiconductor laser beam-emitting means whose output is controllable.

6. The photothermal spectroscopic analyzer according to claim 1, wherein a wavelength of the excitation light is in a range of 400 to 700 nm.

7. The photothermal spectroscopic analyzer according to claim 1, wherein the light source of the excitation light is a semiconductor laser beam-emitting means which is adapted to be electrically modulated.

8. The photothermal spectroscopic analyzer according to claim 1, further comprising signal extraction means which extracts signals by synchronous detection.

9. The photothermal spectroscopic analyzer according to claim 1, further comprising means for adjusting a distance between at least one of focal points of the excitation light and the probe light; and a sample cell which contains the sample, wherein the adjusting means utilizes light reflected from the sample cell.

10. The photothermal spectroscopic analyzer according to claim 2, wherein the light source of the excitation light and the light source of the probe light are semiconductor laser beam-emitting means which output is controllable.

11. The photothermal spectroscopic analyzer according to claim 2, wherein a wavelength of the excitation light is in a range of 400 to 700 nm.

12. The photothermal spectroscopic analyzer according to claim 2, wherein the light source of the excitation light is a semiconductor laser beam-emitting means which is adapted to be electrically modulated.

13. The photothermal spectroscopic analyzer according to claim 2, further comprising signal extraction means which extracts signals by synchronous detection.

14. The photothermal spectroscopic analyzer according to claim 2, further comprising means for adjusting a distance between at least one of focal points of the excitation light and the probe light; and a sample cell which contains the sample, wherein the adjusting means utilizes light reflected from the sample cell.

15. A photothermal spectroscopic analyzer in which a probe light is incident on a thermal lens generated in a sample by incidence of an excitation light, and for analyzing the sample on the basis of a change in the probe light by the thermal lens in that case, comprising:

a light source of the excitation light which comprises semiconductor laser beam-emitting means;

a light source of the probe light which comprises another semiconductor laser beam-emitting means, wherein a condenser lens which focuses the excitation light in the sample and a condenser lens which focuses the probe light in the thermal lens are made to be a common lens;

at least one detection means of detecting a change in the probe light by the thermal lens;

means for adjusting a distance between at least one of focal points of the excitation light and the probe light; and a sample cell which contains the sample, wherein the adjusting means utilizes light reflected from the sample cell, wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm.

16. A photothermal spectroscopic analyzer in which a probe light is incident on a thermal lens generated in a sample by incidence of an excitation light, and for analyzing the sample on the basis of a change in the probe light by the thermal lens in that case, comprising:

a light source of the excitation light which comprises semiconductor laser beam-emitting means;

a light source of the probe light which comprises another semiconductor laser beam-emitting means, wherein a condenser lens which focuses the excitation light in the sample and a condenser lens which focuses the probe light in the thermal lens are made to be a common lens;

at least one detection means of detecting a change in the probe light by the thermal lens;

at least one collimator lens where a semiconductor laser beam emitted from the light source of the excitation light is incident, or where a semiconductor laser beam emitted from the light source of the probe light is incident; and rounding means between at least the light source of the excitation light or the light source of the probe light, wherein the condenser lens brings a cross sectional geometry of at least one semiconductor laser beam emitted from the light sources into approximately the shape of a circles, wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

17. A photothermal spectroscopic analyzer in which a probe light is incident on a thermal lens generated in a sample by incidence of an excitation light, and for analyzing the sample on the basis of a change in the probe light by the thermal lens in that case, comprising:

a light source of the excitation light which comprises semiconductor laser beam-emitting means;

a light source of the probe light which comprises another semiconductor laser beam-emitting means, wherein a condenser lens which focuses the excitation light in the sample and a condenser lens which focuses the probe light in the thermal lens are made to be a common lens;

at least one detection means of detecting a change in the probe light by the thermal lens;

at least one collimator lens where a semiconductor laser beam emitted from the light source of the excitation light is incident, or where a semiconductor laser beam emitted from the light source of the probe light is incident; and astigmatism correction means between at least the light source of the excitation light or the light source of the probe light, wherein the condenser lens reduces the astigmatism of at least one of the semiconductor laser beams emitted from the light sources, wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

18. A photothermal spectroscopic analyzer in which a probe light is incident on a thermal lens generated in a sample by incidence of an excitation light, and for analyzing the sample on the basis of a change in the probe light by the thermal lens in that case, comprising:

a light source of the excitation light which comprises semiconductor laser beam-emitting means;

a light source of the probe light which comprises another semiconductor laser beam-emitting means, wherein a condenser lens which focuses the excitation light in the sample and a condenser lens which focuses the probe light in the thermal lens are made to be a common lens;

at least one detection means of detecting a change in the probe light by the thermal lens;

at least one collimator lens where a semiconductor laser beam emitted from the light source of the excitation light is incident, or where a semiconductor laser beam emitted from the light source of the probe light is incident;

means for adjusting a distance between at least one of focal points of the excitation light and the probe light; and a sample cell which contains the sample, wherein the adjusting means utilizes light reflected from the sample cell, wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

19. A photothermal spectroscopic analyzer in which a probe light is incident on a thermal lens generated in a sample by incidence of an excitation light, and for analyzing the sample on the basis of a change in the probe light by the thermal lens in that case, comprising:

a light source of the excitation light which comprises semiconductor laser beam-emitting means;

a light source of the probe light which comprises another semiconductor laser beam-emitting means, wherein a condenser lens which focuses the excitation light in the sample and a condenser lens which focuses the probe light in the thermal lens are made to be a common lens;

at least one detection means of detecting a change in the probe light by the thermal lens;

at least one collimator lens where a semiconductor laser beam emitted from the light source of the excitation light is incident, or where a semiconductor laser beam emitted from the light source of the probe light is incident;

focal point adjustment means in the at least one collimator lens for adjusting a focal point of the semiconductor laser beam by changing a distance in the direction of an optical axis between the at least one collimator lens and the light source of the excitation light or the probe light; and rounding means between at least the light source of the excitation light or the light source of the probe light, wherein the condenser lens brings a cross sectional geometry of at least one semiconductor laser beam emitted from the light sources into approximately the shape of a circle, wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

20. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens;
at least one detection means of detecting a change in the probe light by the thermal lens;
at least one collimator lens where a semiconductor laser beam emitted from the light source of the excitation light is incident, or where a semiconductor laser beam emitted from the light source of the probe light is incident;
focal point adjustment means in the at least one collimator lens for adjusting a focal point of the semiconductor laser beam by changing a distance in the direction of an optical axis between the at least one collimator lens and the light source of the excitation light or the probe light; and
astigmatism correction means between at least the light source of the excitation light or the light source of the probe light, wherein the condenser lens reduces the astigmatism of at least one of the semiconductor laser beams emitted from the light sources,
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm.

21. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens; and
at least one detection means of detecting a change in the probe light by the thermal lens;
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm, wherein the light source of the excitation light and the light source of the probe light are semiconductor laser beam-emitting means whose output is controllable, and wherein a wavelength of the excitation light is in a range of 400 to 700 nm.

22. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens; and
at least one detection means of detecting a change in the probe light by the thermal lens;
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 μm, wherein the light source of the excitation light and the light source of the probe light are semiconductor laser beam-emitting means whose output is controllable, and wherein the light source of the excitation light is a semiconductor laser beam-emitting means which is adapted to be electrically modulated.

23. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens;
at least one detection means of detecting a change in the probe light by the thermal lens; and
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, and wherein the light source of the excitation light and the light source of the probe light are semiconductor laser beam-emitting means whose output is controllable.

24. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens;
at least one detection means of detecting a change in the probe light by the thermal lens;
means for adjusting a distance between at least one of focal points of the excitation light and the probe light; and
a sample cell which contains the sample, wherein the adjusting means utilizes light reflected from the sample cells,
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, and wherein the light source of the excitation light and the light source of the probe light are semiconductor laser beam-emitting means whose output is controllable.

25. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens; and
at least one detection means of detecting a change in the probe light by the thermal lens;
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, wherein a wavelength of the excitation light is in a range of 400 to 700 nm, and wherein the light source of the excitation light is a semiconductor laser beam-emitting means which is adapted to be electrically modulated.

26. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens;
at least one detection means of detecting a change in the probe light by the thermal lens; and
signal extraction means which extracts signals by synchronous detection,
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, and wherein a wavelength of the excitation light is in a range of 400 to 700 nm.

27. A photothermal spectroscopic analyzer in which a probe light is incident on a thermal lens generated in a sample by incidence of an excitation light, and for analyzing the sample on the basis of a change in the probe light by the thermal lens in that case, comprising:
a light source of the excitation light which comprises semiconductor laser beam-emitting means;
a light source of the probe light which comprises another semiconductor laser beam-emitting means, wherein a condenser lens which focuses the excitation light in the sample and a condenser lens which focuses the probe light in the thermal lens are made to be a common lens;
at least one detection means of detecting a change in the probe light by the thermal lens;
means for adjusting a distance between at least one of focal points of the excitation light and the probe light; and
a sample cell which contains the sample, wherein the adjusting means utilizes light reflected from the sample cell,
wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, and wherein a wavelength of the excitation light is in a range of 400 to 700 nm.

28. A photothermal spectroscopic analyzer in which a probe light is incident on a thermal lens generated in a sample by incidence of an excitation light, and for analyzing the sample on the basis of a change in the probe light by the thermal lens in that case, comprising:
- a light source of the excitation light which comprises semiconductor laser beam-emitting means;
- a light source of the probe light which comprises another semiconductor laser beam-emitting means, wherein a condenser lens which focuses the excitation light in the sample and a condenser lens which focuses the probe light in the thermal lens are made to be a common lens;
- at least one detection means of detecting a change in the probe light by the thermal lens; and signal extraction means which extracts signals by synchronous detection,
- wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, and wherein a light source of the excitation light is a semiconductor laser beam-emitting means which is adapted to be electrically modulated.

29. A photothermal spectroscopic analyzer in which a probe light is incident on a thermal lens generated in a sample by incidence of an excitation light, and for analyzing the sample on the basis of a change in the probe light by the thermal lens in that case, comprising:
- a light source of the excitation light which comprises semiconductor laser beam-emitting means;
- a light source of the probe light which comprises another semiconductor laser beam-emitting means, wherein a condenser lens which focuses the excitation light in the sample and a condenser lens which focuses the probe light in the thermal lens are made to be a common lens;
- at least one detection means of detecting a change in the probe light by the thermal lens;
- means for adjusting a distance between at least one of focal points of the excitation light and the probe light; and
- a sample cell which contains the sample, wherein the adjusting means utilizes light reflected from the sample cell,
- wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm, and wherein a light source of the excitation light is a semiconductor laser beam-emitting means which is adapted to be electrically modulated.

30. A photothermal spectroscopic analyzer in which a probe light is incident on a thermal lens generated in a sample by incidence of an excitation light, and for analyzing the sample on the basis of a change in the probe light by the thermal lens in that case, comprising:
- a light source of the excitation light which comprises semiconductor laser beam-emitting means;
- a light source of the probe light which comprises another semiconductor laser beam-emitting means, wherein a condenser lens which focuses the excitation light in the sample and a condenser lens which focuses the probe light in the thermal lens are made to be a common lens;
- at least one detection means of detecting a change in the probe light by the thermal lens;
- signal extraction means which extracts signals by synchronous detection;
- means for adjusting a distance between at least one of focal points of the excitation light and the probe light; and
- a sample cell which contains the sample, wherein the adjusting means utilizes light reflected from the sample cell,
- wherein, when a transmission means, for allowing a part of the probe light which is changed by the thermal lens transmit, is provided between the sample and the at least one detection means, a distance in a direction of an optical axis between the transmission means and the sample is set at 10 cm or less, and a distance in the direction of an optical axis between the at least one detection means and the sample is set at 10 cm or less when a transmission means is not provided, and further a beam diameter in focal points of the excitation light and the probe light which are focused with the condenser lens, is 0.2 to 50 µm.

* * * * *

UNITED STATES PATENT AND TRADEMARK OFFICE
CERTIFICATE OF CORRECTION

PATENT NO. : 7,036,979 B2 Page 1 of 1
APPLICATION NO. : 10/181267
DATED : May 2, 2006
INVENTOR(S) : Kazuma Mawatari It is certified that error appears in the above-identified patent and that said Letters Patent is hereby corrected as shown below:

column 29, line 25, "cells," should read --cell,--.

column 31, line 11, "circles," should read --circle,--.

column 35, line 27, "cells," should read --cell,--.

Signed and Sealed this

Twenty-ninth Day of August, 2006

JON W. DUDAS
*Director of the United States Patent and Trademark Office*